United States Patent
Fukushima et al.

(10) Patent No.: US 11,510,630 B2
(45) Date of Patent: Nov. 29, 2022

(54) DISPLAY CONTROL APPARATUS, IMAGE DISPLAY METHOD, AND NON-TRANSITORY COMPUTER-READABLE MEDIUM

(71) Applicant: CANON KABUSHIKI KAISHA, Tokyo (JP)

(72) Inventors: Satoru Fukushima, Yokohama (JP); Hiroshi Abe, Yokohama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 407 days.

(21) Appl. No.: 16/500,279

(22) PCT Filed: May 2, 2018

(86) PCT No.: PCT/JP2018/017479
§ 371 (c)(1),
(2) Date: Oct. 2, 2019

(87) PCT Pub. No.: WO2018/207692
PCT Pub. Date: Nov. 15, 2018

(65) Prior Publication Data
US 2021/0113161 A1    Apr. 22, 2021

(30) Foreign Application Priority Data

May 11, 2017    (JP) .............................. JP2017-094994

(51) Int. Cl.
*G09G 5/02*    (2006.01)
*A61B 5/00*    (2006.01)
(Continued)

(52) U.S. Cl.
CPC ............ *A61B 5/7425* (2013.01); *A61B 5/004* (2013.01); *A61B 5/0035* (2013.01);
(Continued)

(58) Field of Classification Search
CPC .... G09G 5/02; G09G 5/06; G09G 2320/0666; G09G 2340/06; G09T 11/001
(Continued)

(56) References Cited

U.S. PATENT DOCUMENTS 6,283,918 B1    9/2001 Kanda
2011/0196237 A1*    8/2011 Pelissier ................ A61B 8/467
                                                                 600/454

(Continued)

FOREIGN PATENT DOCUMENTS

JP        2012-213609 A    11/2012
JP        2013-233386 A    11/2013
WO        2018116963 A1    6/2018

*Primary Examiner* — Gordon G Liu
(74) *Attorney, Agent, or Firm* — Canon U.S.A., Inc. IP Division

(57) ABSTRACT

The present invention provides an image display method with which a structure of an imaging object can be easily understood on the basis of volume data. An image display method according to an aspect of the present invention includes obtaining photoacoustic image data, generating a first photoacoustic image corresponding to a first spatial region on the basis of photoacoustic image data and a second photoacoustic image corresponding to a second spatial region having a different thickness in a viewing direction of rendering from a thickness of the first spatial region and having a spatial region overlapped with the first spatial region on the basis of the photoacoustic image data, and generating and displaying a parallel image in which the first photoacoustic image and the second photoacoustic image are arranged side by side.

22 Claims, 20 Drawing Sheets

(51) Int. Cl.
*A61B 5/055* (2006.01)
*A61B 6/03* (2006.01)
*A61B 6/00* (2006.01)
*A61B 8/08* (2006.01)
*A61B 8/14* (2006.01)
*A61B 8/00* (2006.01)
*G06T 11/00* (2006.01)
*G06T 11/60* (2006.01)

(52) U.S. Cl.
CPC ............ *A61B 5/0095* (2013.01); *A61B 5/055* (2013.01); *A61B 5/4312* (2013.01); *A61B 5/489* (2013.01); *A61B 6/032* (2013.01); *A61B 6/037* (2013.01); *A61B 6/463* (2013.01); *A61B 6/502* (2013.01); *A61B 6/504* (2013.01); *A61B 8/0825* (2013.01); *A61B 8/0891* (2013.01); *A61B 8/14* (2013.01); *A61B 8/463* (2013.01); *A61B 8/485* (2013.01); *G06T 11/001* (2013.01); *G06T 11/60* (2013.01); *G06T 2210/41* (2013.01)

(58) Field of Classification Search
USPC .......................................................... 345/589
See application file for complete search history.

(56) References Cited

U.S. PATENT DOCUMENTS

| | | | |
|---|---|---|---|
| 2013/0022222 A1* | 1/2013 | Zschau | G03H 1/0808 359/9 |
| 2014/0093029 A1 | 4/2014 | Masumoto | |
| 2014/0228860 A1* | 8/2014 | Steines | A61B 34/30 606/130 |
| 2014/0350358 A1* | 11/2014 | Oikawa | A61B 5/6843 600/407 |
| 2015/0334308 A1 | 11/2015 | Abe | |
| 2016/0091415 A1 | 3/2016 | Furukawa | |
| 2016/0117857 A1* | 4/2016 | State | A61B 34/20 345/420 |
| 2017/0095155 A1 | 4/2017 | Nakajima | |

* cited by examiner

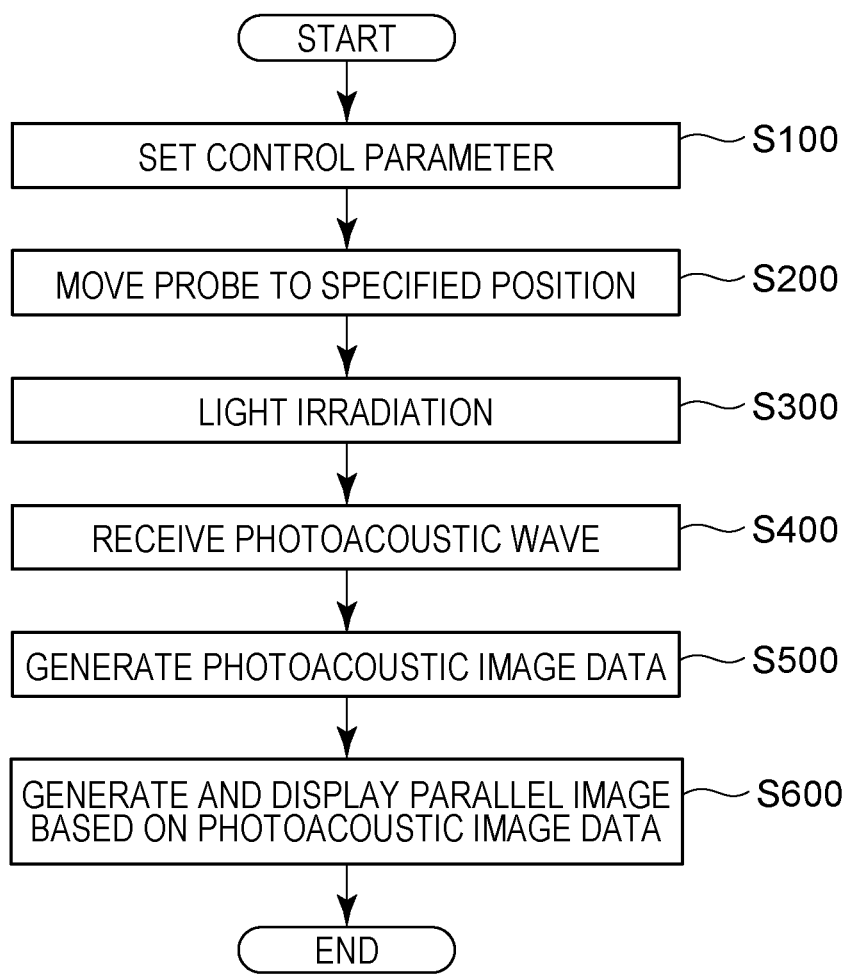

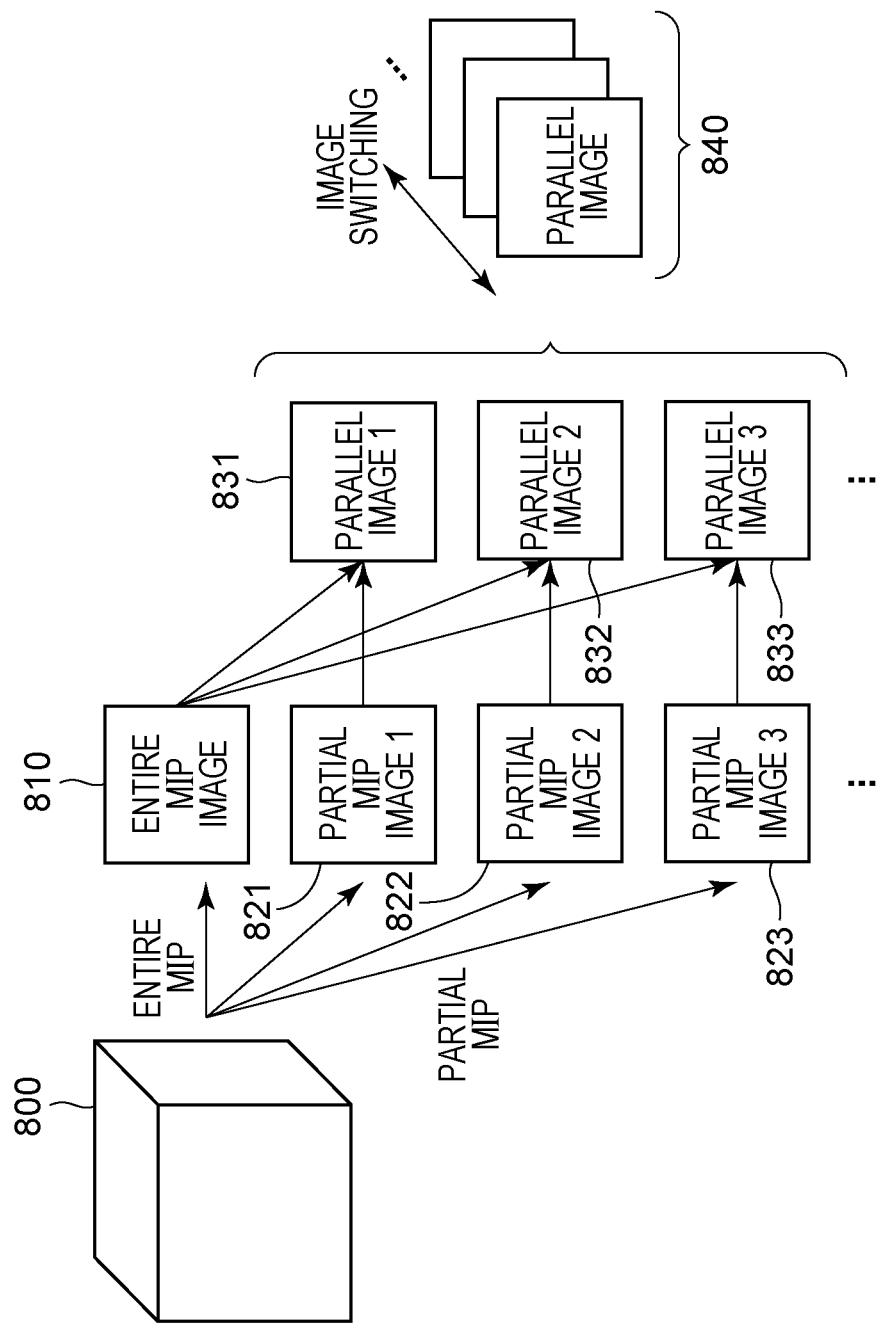

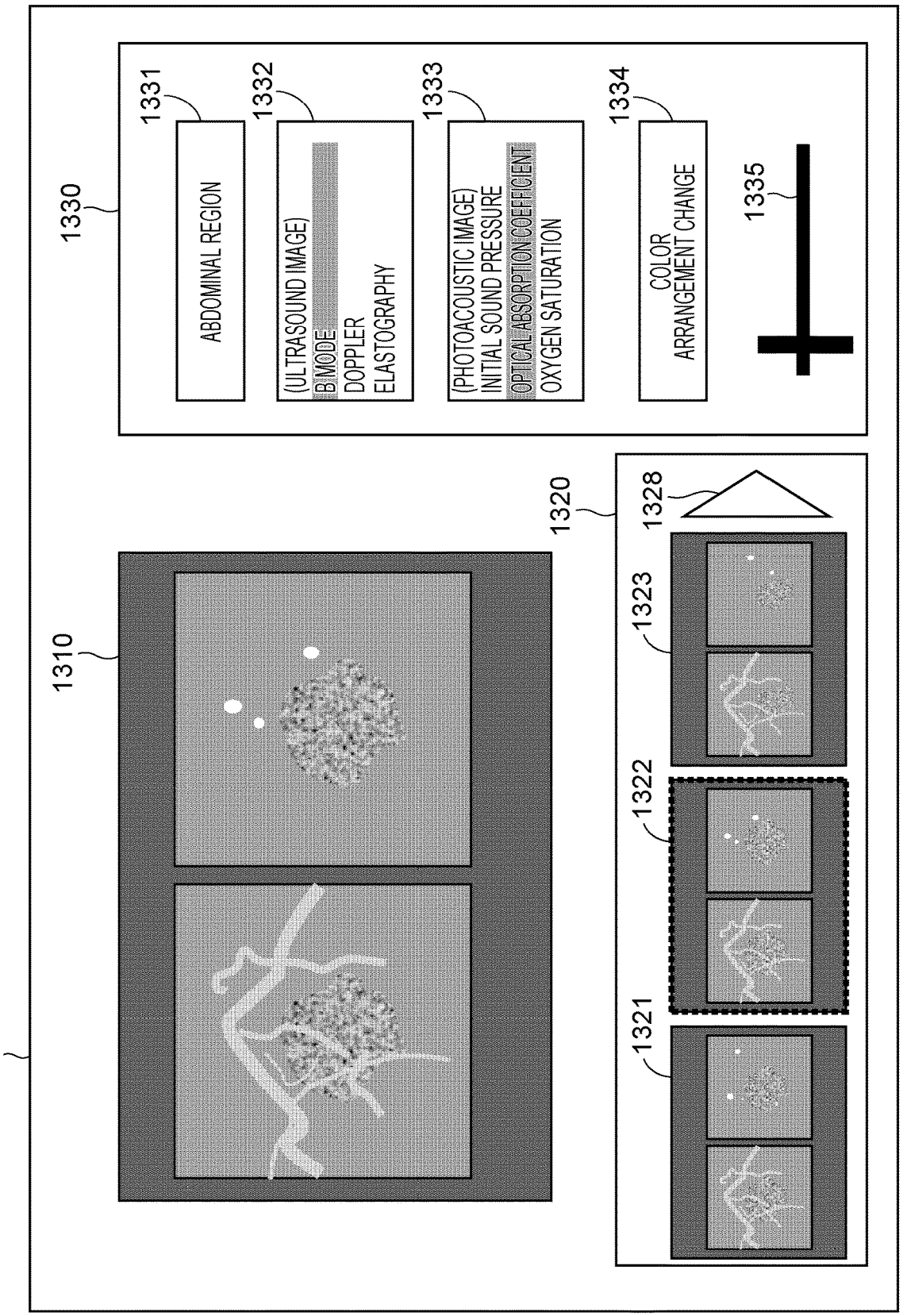

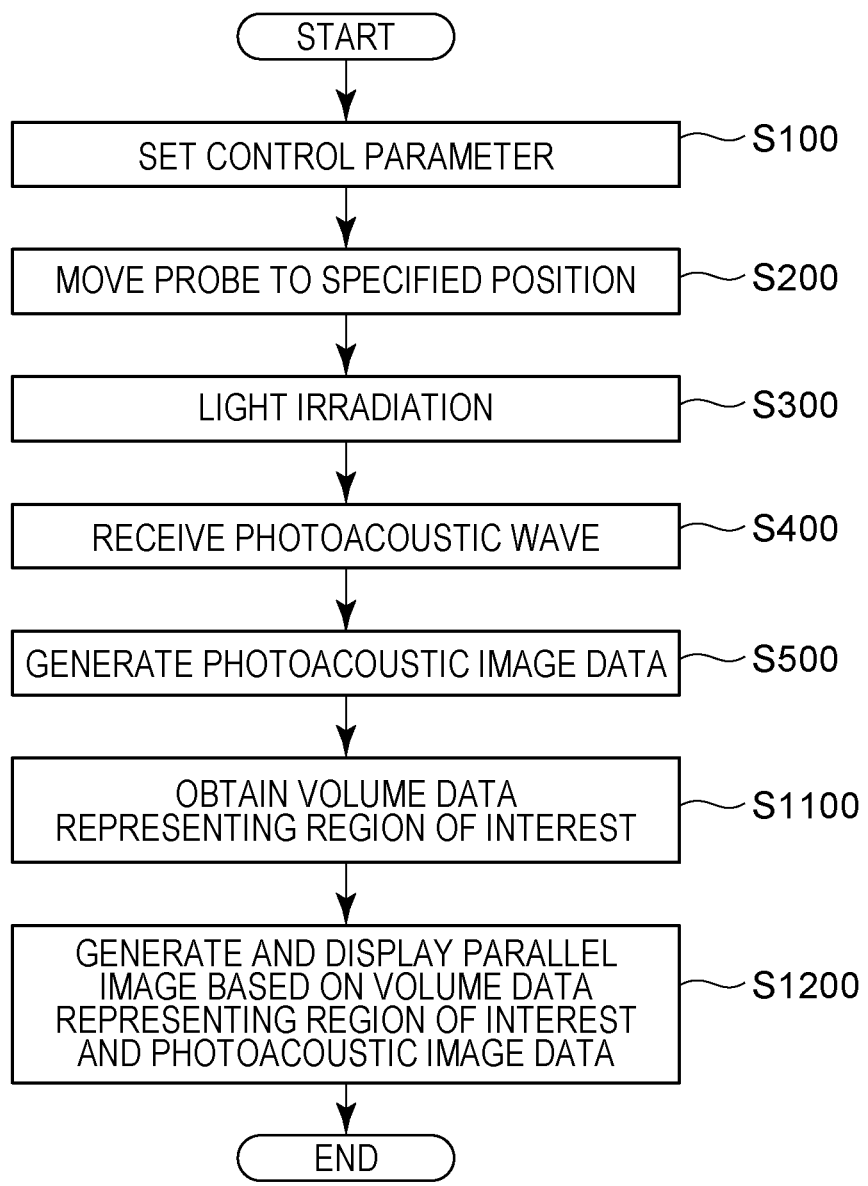

DISPLAY CONTROL APPARATUS, IMAGE DISPLAY METHOD, AND NON-TRANSITORY COMPUTER-READABLE MEDIUM

TECHNICAL FIELD

The present invention relates to an image display method based on volume data.

BACKGROUND ART

Photoacoustic imaging or the like has been proposed as an imaging technology for displaying an image based on volume data generated by a medical image diagnosis apparatus (modality). The photoacoustic imaging is the imaging technology which with a photoacoustic wave generated from an optical absorber irradiated with light is received, and a spatial distribution of the optical absorber can be imaged. When the photoacoustic imaging is applied to a living body, the optical absorber such as a blood vessel including hemoglobin can be imaged.

PTL 1 describes that photoacoustic image data in a three-dimensional (3D) space (XYZ space) is generated by using a photoacoustic imaging principle, and a tomographic image of the photoacoustic image data (volume data) on a certain plane is displayed. PTL 1 describes that a plurality of ultrasonic transducers including probes arranged in an X-direction are provided, and a tomographic image of the photoacoustic image data in an XZ cross section is displayed in a case where scanning of the probes is performed in a Y-direction.

CITATION LIST

Patent Literature

[PTL 1]
Japanese Patent Laid-Open No. 2013-233386

SUMMARY OF INVENTION

Solution to Problem

When an image of one cross section of volume data is displayed, it may be difficult to understand a structure of an imaging object in some cases.

In view of the above, the present invention provides an image display method based on the volume data with which the structure of the imaging object can be easily understood.

An image display method according to an aspect of the present invention includes obtaining photoacoustic image data, generating a first photoacoustic image corresponding to a first spatial region on the basis of the photoacoustic image data, generating a second photoacoustic image corresponding to a second spatial region having a different thickness in a viewing direction of rendering from a thickness of the first spatial region and having a spatial region overlapped with the first spatial region on the basis of the photoacoustic image data, and generating and displaying a parallel image in which the first photoacoustic image and the second photoacoustic image are arranged side by side.

Further features of the present invention will become apparent from the following description of exemplary embodiments with reference to the attached drawings.

BRIEF DESCRIPTION OF DRAWINGS

FIG. 6 is a flow chart of the image display method according to the first exemplary embodiment.

FIG. 8 is a conceptual diagram illustrating a generation method for a parallel image corresponding to a plurality of spatial regions according to the first exemplary embodiment.

FIG. 13 is a schematic diagram illustrating a graphical user interface (GUI) according to the second exemplary embodiment.

FIG. 14 is a flow chart of the image display method according to a third exemplary embodiment.

DESCRIPTION OF EMBODIMENTS

An exemplary embodiment of the present invention is an invention related to a method of displaying an image based on volume data representing image data in a three-dimensional space. In particular, the exemplary embodiment of the present invention can be preferably applied to a method of displaying an image based on photoacoustic image data as volume data derived from a photoacoustic wave generated by light irradiation. The photoacoustic image data is the volume data representing a three-dimensional spatial distribution of at least one piece of object information such as a generated sound pressure (initial sound pressure), an optical absorption energy density, and an optical absorption coefficient of the photoacoustic wave, a concentration of a material constituting the object (such as an oxygen saturation), and the like.

Figure 1A:
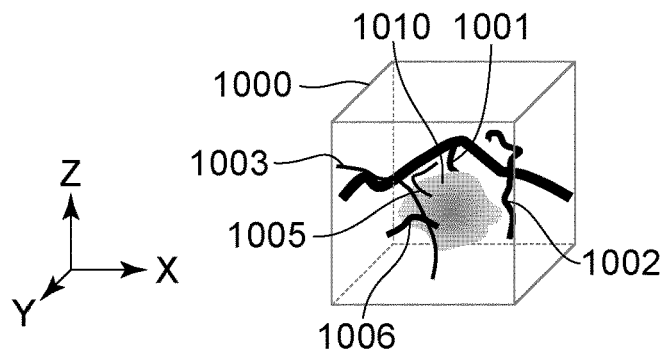
FIG. 1A is a schematic diagram illustrating an image display method according to a comparative example.
Figure 1B:
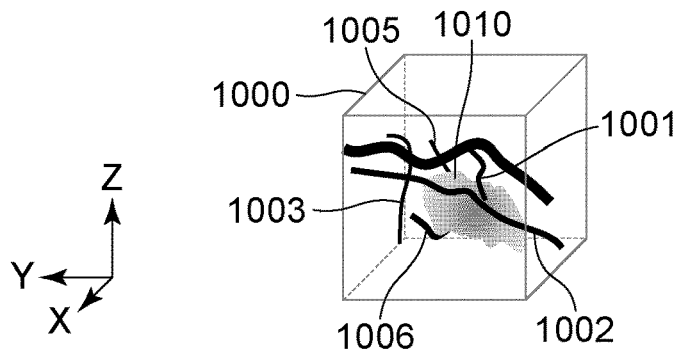
FIG. 1B is a schematic diagram illustrating the image display method according to the comparative example.

FIG. 1A is a schematic diagram of photoacoustic image data 1000 representing volume data generated on the basis of a reception signal of a photoacoustic wave. The photoacoustic image data 1000 illustrated in FIG. 1A includes image data corresponding to blood vessels 1001, 1002, 1003, 1005, and 1006. A schematic diagram corresponding to a tumor 1010 is displayed for convenience although this is not the image data included in the photoacoustic image data 1000. FIG. 1B illustrates the photoacoustic image data 1000 illustrated in FIG. 1A after being rotated by 90° about a Z-axis direction.

As illustrated in FIGS. 1A to 1F, the blood vessels 1001, 1005, and 1006 are blood vessels intruding into the tumor 1010. On the other hand, the blood vessels 1002 and 1003 are blood vessels that are not intruding into the tumor 1010.

Figure 1C:
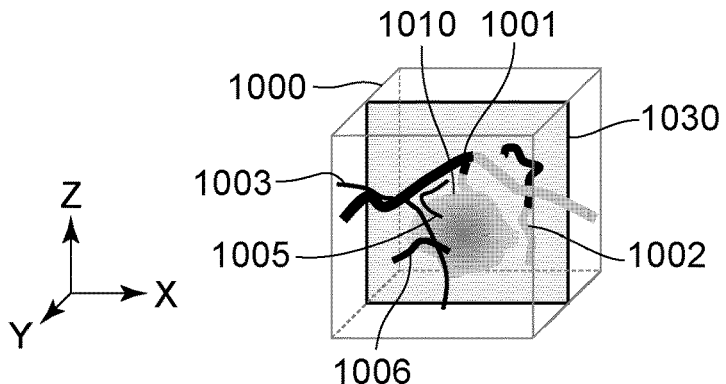
FIG. 1C is a schematic diagram illustrating the image display method according to the comparative example.
Figure 1D:
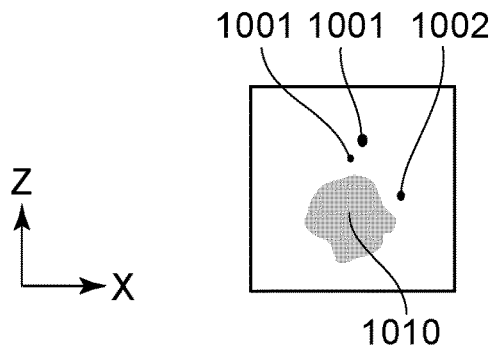
FIG. 1D is a schematic diagram illustrating the image display method according to the comparative example.

Here, a case will be considered as a comparative example where photoacoustic image data of a cross section 1030 illustrated in FIG. 1C is imaged. FIG. 1D illustrates a tomographic image of the photoacoustic image data of the cross section 1030. In FIG. 1D too, a region of the tumor 1010 intersecting with the cross section 1030 is illustrated for convenience. A part of the blood vessels 1001 and 1002 intersecting with the cross section 1030 is displayed in the tomographic image. However, it is difficult to understand links of the blood vessels, that is, a structure of the imaging object, by simply looking at this tomographic image. For this reason, in a case where a position of the cross section is changed to check the tomographic image, it is difficult to perform observation while supposing whether or not blood vessel images displayed on the respective tomographic images are advancing towards the tumor 1010.

Figure 1E:
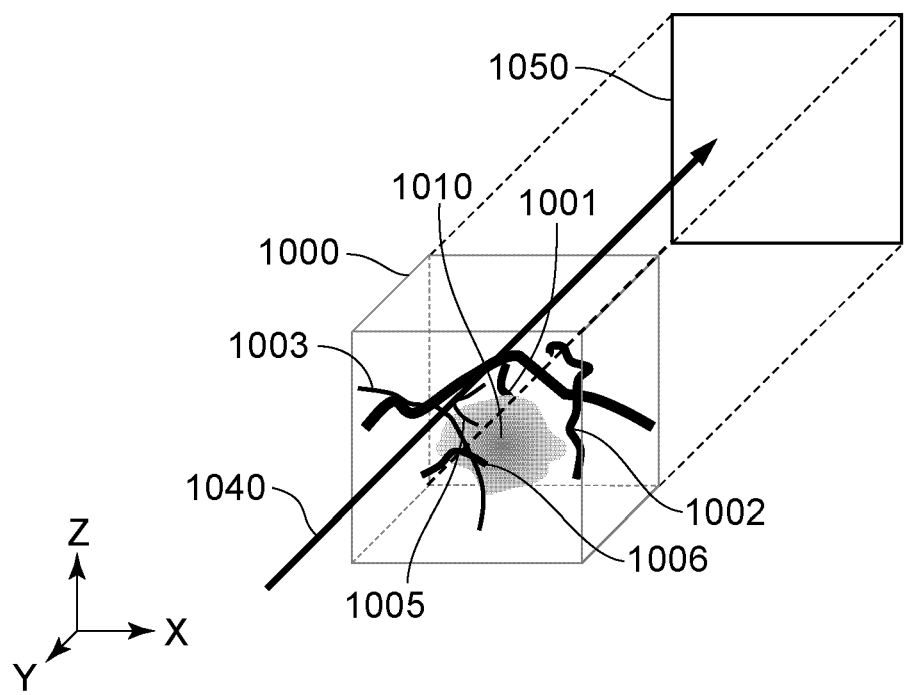
FIG. 1E is a schematic diagram illustrating the image display method according to the comparative example.
Figure 1F:
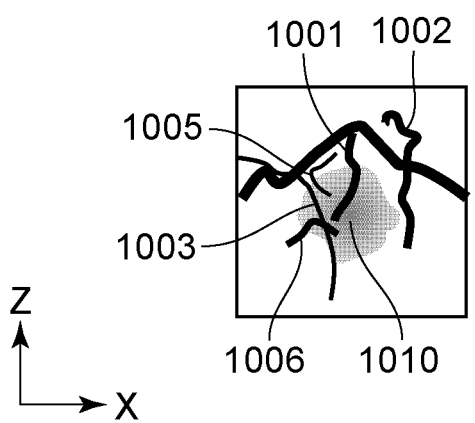
FIG. 1F is a schematic diagram illustrating the image display method according to the comparative example.

On the other hand, a case will be considered as another comparative example where the photoacoustic image data is projected in a Y-axis direction to be displayed. In this comparative example, an example will be described where a projected image is displayed by performing maximum intensity projection. FIG. 1F illustrates a projected image generated by projecting the photoacoustic image data in a viewing direction 1040 (Y-axis direction) as illustrated in FIG. 1E. That is, FIG. 1F illustrates the image obtained by performing the maximum intensity projection of the photoacoustic image data 1000 on a projection surface 1050. In FIG. 1E too, the tumor 1010 is illustrated for convenience. It may look as if both the blood vessels 1001 and 1003 intrude into the tumor 1010 in the projected image. However, as illustrated in FIG. 1A and FIG. 1B, the blood vessel 1003 is a blood vessel that is not intruding into the tumor 1010. In this manner, the projected image obtained by projecting the photoacoustic image data loses information of a depth direction (projection direction). For this reason, there is a possibility that a user may erroneously recognize that the blood vessel 1003 that is not actually intruding into the tumor 1010 intrudes into the tumor 1010.

According to the image display method described in the comparative example, it is difficult to understand the structure of the imaging object from the above-described reason. In view of the above, while this issue is taken into account, the inventor of the present invention has found an image display method with which it is possible to easily understand both connectivity of the structure of the imaging object and a local structure. That is, the inventor of the present invention has devised an image display method of arranging a first image corresponding to a first spatial region and a second image corresponding to a second spatial region side by side to be displayed. The first image is equivalent to an image representing volume data corresponding to the first spatial region. That is, the first image is equivalent to an image obtained by performing rendering of the volume data corresponding to the first spatial region. The second image is equivalent to an image representing volume data corresponding to the second spatial region. That is, the second image is equivalent to an image obtained by performing rendering of the volume data corresponding to the second spatial region. In addition, the inventor of the present invention has devised that the second spatial region is set to have a different thickness in a viewing direction of the rendering from a thickness of the first spatial region and also having a spatial region overlapped with the first spatial region in this image display method. With this configuration, the user can understand both connectivity of the structure of the imaging object and the local structure at the same time.

Figure 2A:
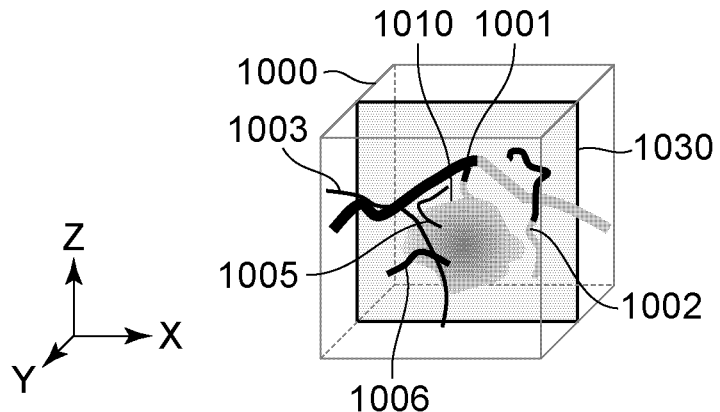
FIG. 2A is a schematic diagram illustrating an image display method according to an exemplary embodiment of the present invention.
Figure 2B:
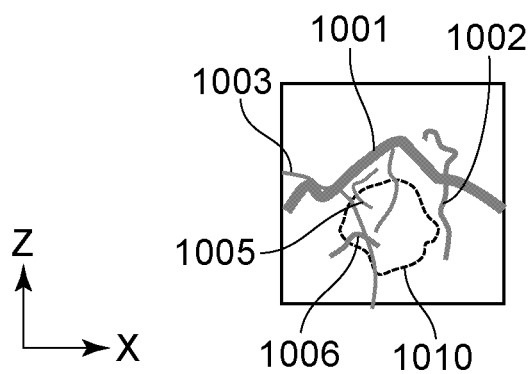
FIG. 2B is a schematic diagram illustrating the image display method according to the exemplary embodiment of the present invention.
Figure 2C:
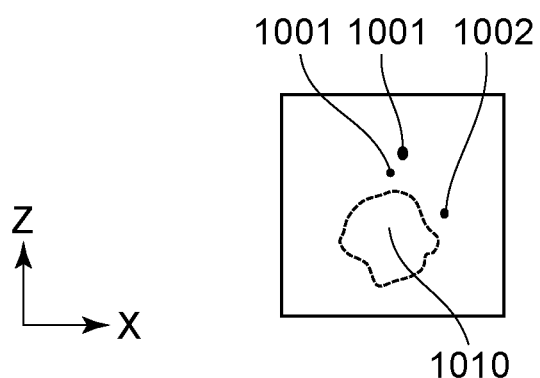
FIG. 2C is a schematic diagram illustrating the image display method according to the exemplary embodiment of the present invention.

According to an exemplary embodiment of the present invention, the projected image (first photoacoustic image) is generated by performing the maximum intensity projection of the photoacoustic image data 1000 illustrated in FIG. 2A in the Y-axis direction (FIG. 2B). The tomographic image (second photoacoustic image) representing the photoacoustic image data of the cross section 1030 is generated (FIG. 2C). Subsequently, an image in which the projected image illustrated in FIG. 2B and the tomographic image illustrated in FIG. 2C are arranged side by side is displayed. It should be noted that, in FIG. 2B and FIG. 2C, the region of the tumor 1010 existing in the cross section 1030 is displayed for convenience. According to this image display method, it is possible to easily understand whether or not the blood vessel existing in the cross section 1030 is a blood vessel that may possibly be intruding into the tumor. In addition, it is possible to easily understand whether or not the blood vessel is a blood vessel that approaches the tumor in a case where the tomographic images are fed and displayed by changing the position of the cross section 1030 too.

Figure 2D:
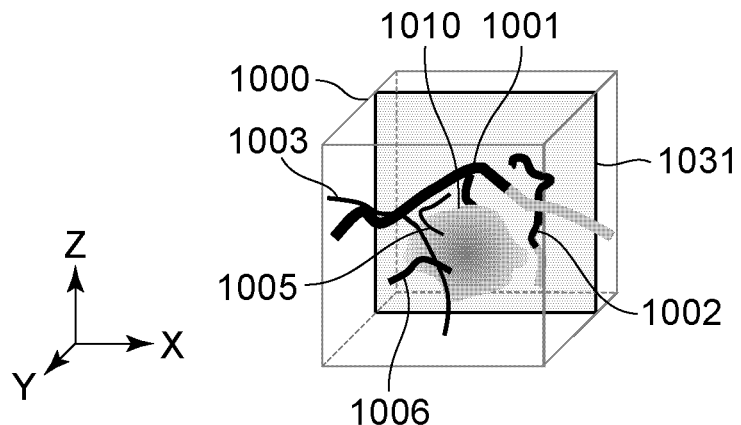
FIG. 2D is a schematic diagram illustrating the image display method according to the exemplary embodiment of the present invention.
Figure 2E:
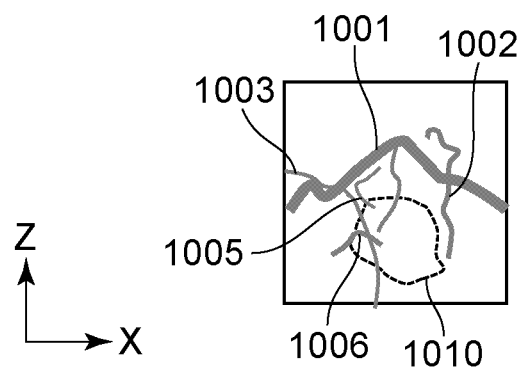
FIG. 2E is a schematic diagram illustrating the image display method according to the exemplary embodiment of the present invention.
Figure 2F:
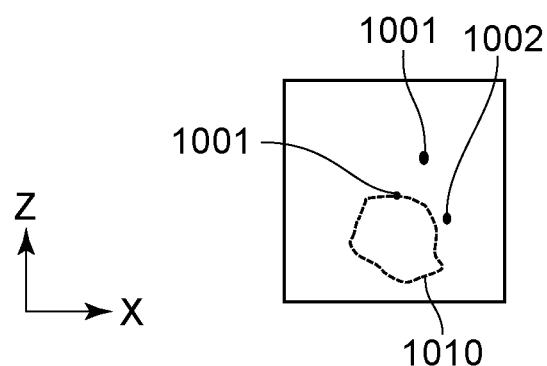
FIG. 2F is a schematic diagram illustrating the image display method according to the exemplary embodiment of the present invention.

Next, a case will be described where the cross section with respect to the photoacoustic image data 1000 is changed from the cross section 1030 illustrated in illustrated in FIG. 2A to a cross section 1031 illustrated in FIG. 2D. FIG. 2E illustrates a projected image generated by performing the maximum intensity projection of the photoacoustic image data 1000 illustrated in FIG. 2D in the Y-axis direction. FIG. 2F illustrates a tomographic image representing the photoacoustic image data 1000 of the cross section 1031 illustrated in FIG. 2D. Then, an image in which the projected image illustrated in FIG. 2E and the tomographic image illustrated in FIG. 2F are arranged side by side is displayed.

A plurality of parallel images of the projected image and the tomographic image are generated by the above-described method, and these parallel images are switched to be displayed. When the display is performed in the above-described manner, while the user understands the overall structure of the blood vessel 1001 by referring to the projected image illustrated in FIG. 2B or FIG. 2E, the user can confirm that the blood vessel 1001 is a blood vessel intruding into the tumor 1010 from the tomographic image illustrated in FIG. 2C or FIG. 2F.

It should be noted that the descriptions are provided while the region of the tumor that does not exist in the photoacoustic image data is illustrated for convenience according to the image display method illustrated in FIGS. 2A to 2F. According to the exemplary embodiment of the present invention, volume data representing a region of interest may be obtained, and an image representing the region of interest corresponding to the cross section 1030 may be displayed by being superimposed on the image illustrated in FIG. 2B, FIG. 2C, FIG. 2E, or FIG. 2F. In addition, according to the exemplary embodiment of the present invention, the tomographic image of the cross section 1030 with regard to volume data obtained by a modality other than a photoacoustic apparatus (such as an ultrasonic diagnosis apparatus, a magnetic resonance imaging (MRI) apparatus, an X-ray computed tomography (CT) apparatus, or a positron-emission tomography (PET) apparatus) may be displayed by being superimposed on the image illustrated in FIG. 2B, FIG. 2C, FIG. 2E, or FIG. 2F. When these pieces of information are displayed by being superimposed on each other, it is possible to easily understand both a positional relationship between an overall structure of the blood vessels included in the photoacoustic image data and the region of interest such as the tumor and a positional relationship between the blood vessels in the cross section and the region of interest such as the tumor.

With regard to the volume data to which the exemplary embodiment of the present invention can be applied, it is possible to apply the exemplary embodiment of the present invention to any volume data obtained by the modality such as the photoacoustic apparatus, the ultrasonic diagnosis apparatus, the MRI apparatus, the X-ray CT apparatus, or the PET apparatus. It should be noted that the exemplary embodiment of the present invention can be preferably applied to the photoacoustic apparatus in particular. In the photoacoustic imaging, unless the acoustic waves are received from all directions, the structure of the imaging object is not completely reconstructed because of an influence of Limited-View. For this reason, there is a possibility that the reconstruction may be performed while the structure such as the blood vessel included in the volume data is interrupted. It is conceivable that the display is performed by projecting a large spatial region of the volume data to perform the display while the above-described interruption of the structure is suppressed. However, as described above with reference to FIG. 1E, it becomes difficult to understand depth information of the imaging object in this case. For example, in a case where it is checked whether or not the blood vessel corresponding to the imaging object is intruding into the tumor, when rendering of the large spatial region is performed, there is a possibility that it may be misidentified that the blood vessel is intruding into the tumor although the blood vessel is not intruding into the tumor.

On the other hand, to suppress the above-described misidentification, it is conceivable that a smaller spatial region is imaged and displayed as illustrated in FIG. 1D. However, in this case, if reproducibility of the structure in the volume data is low, due to a reason that the structure is interrupted halfway through when the images are fed by changing the cross section or the like, it is difficult to understand whether or not the structure is a continuous structure. As a result, there is a possibility that the structure of the imaging object may be misidentified.

From the above-described reason, when the image display method according to the exemplary embodiment of the present invention is applied to the photoacoustic apparatus, it is possible to easily understand both the continuous structure of the imaging object and the local structure in even the photoacoustic apparatus in which it is difficult to obtain the volume data having the high reproducibility of the structure of the imaging object.

Hereinafter, exemplary embodiments of the present invention will be described with reference to the drawings. It should be noted however that dimensions, materials, and shapes of components which will be described below, those relative positions, and the like are to be appropriately changed depending on the configurations and various conditions of the apparatus to which the exemplary embodiments of the present invention are applied, and are not intended to limit the scope of the present invention to the following descriptions.

First Exemplary Embodiment

According to a first exemplary embodiment, an example will be described in which an image based on the photoacoustic image data obtained by the photoacoustic apparatus is displayed. Hereinafter, a configuration of the photoacoustic apparatus according to the present exemplary embodiment and an information processing method will be described.

Figure 3:
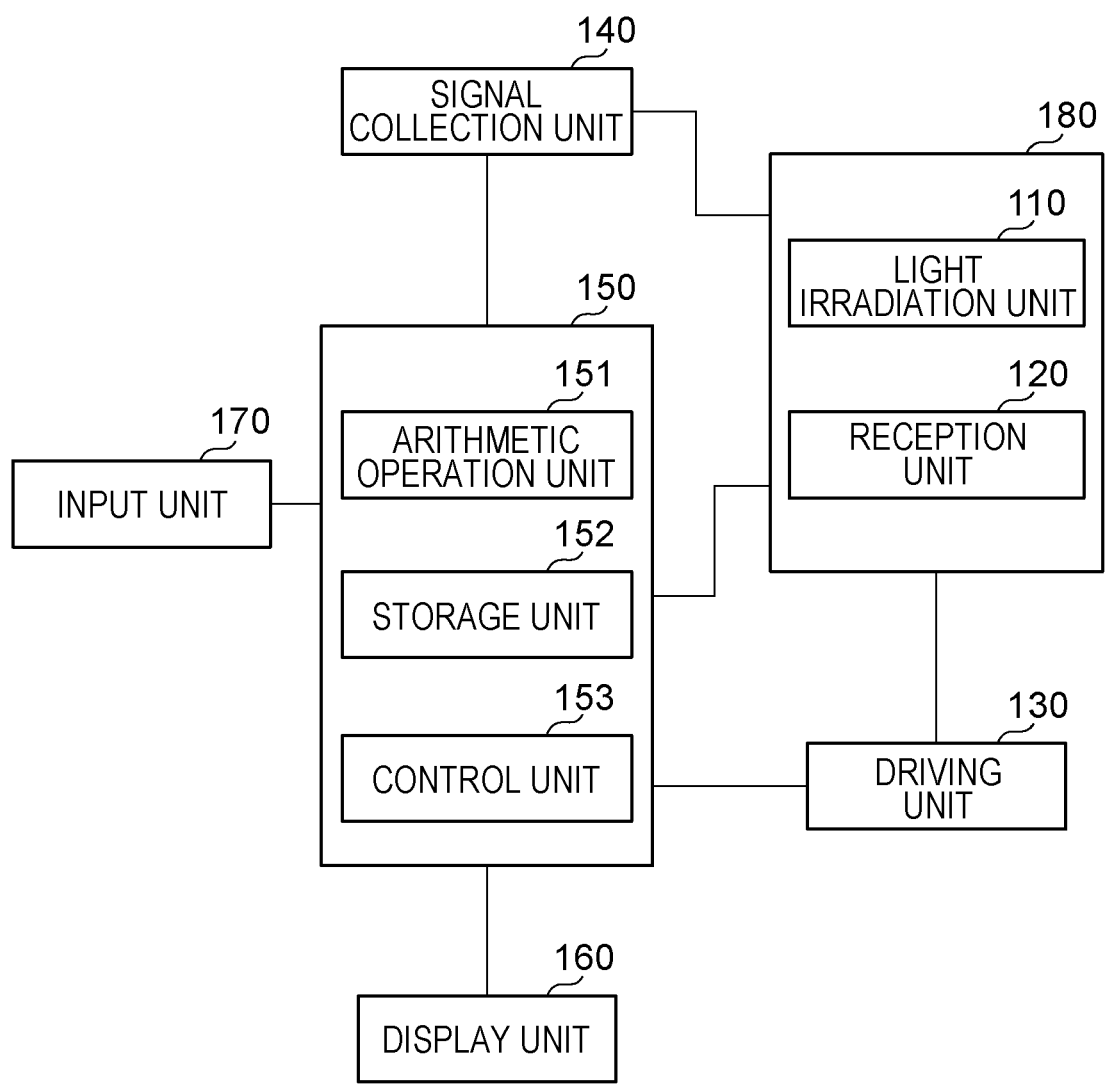
FIG. 3 is a block diagram illustrating a photoacoustic apparatus according to a first exemplary embodiment.

The configuration of the photoacoustic apparatus according to the present exemplary embodiment will be described with reference to FIG. 3. FIG. 3 is a schematic block diagram of the entirety of the photoacoustic apparatus. The photoacoustic apparatus according to the present exemplary embodiment includes a probe 180 including a light irradiation unit 110 and a reception unit 120, a driving unit 130, a signal collection unit 140, a computer 150, a display unit 160, and an input unit 170.

Figure 4A:
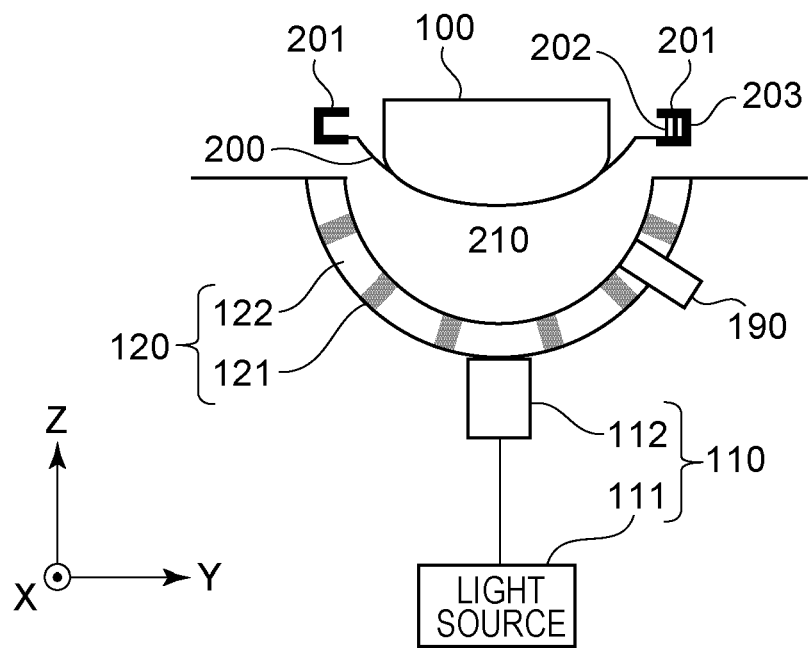
FIG. 4A is a schematic diagram illustrating a probe according to the first exemplary embodiment.
Figure 4B:
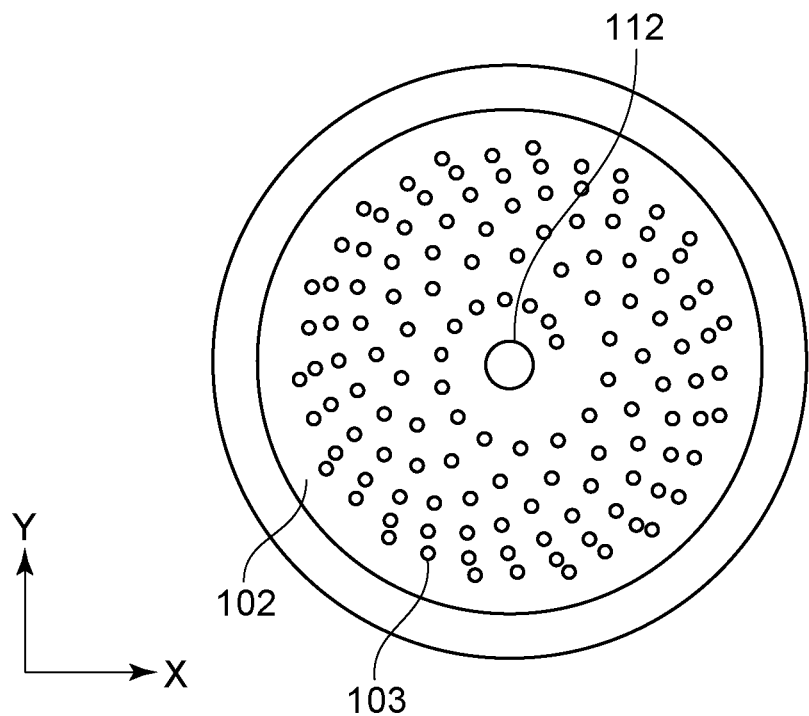
FIG. 4B is a schematic diagram illustrating the probe according to the first exemplary embodiment.

FIGS. 4A and 4B are schematic diagrams of the probe 180 according to the present exemplary embodiment. A measurement object is an object 100. The driving unit 130 drives the light irradiation unit 110 and the reception unit 120 and performs mechanical scanning. The light irradiation unit 110 irradiates the object 100 with light, and an acoustic wave is generated in the object 100. The acoustic wave generated by a photoacoustic effect derived from the light is also referred to as a photoacoustic wave. The reception unit 120 outputs an electric signal (photoacoustic signal) as an analog signal when the photoacoustic wave is received.

The signal collection unit 140 converts the analog signal output from the reception unit 120 into a digital signal to be output to the computer 150. The computer 150 stores the digital signal output from the signal collection unit 140 as signal data derived from an ultrasonic wave or the photoacoustic wave.

The computer 150 generates the volume data (photoacoustic image data) representing a three-dimensional spatial distribution of information (object information) related to the object 100 by performing signal processing on the stored digital signal. In addition, the computer 150 causes the display unit 160 to display an image based on the obtained volume data. A doctor acting as the user can perform the diagnosis by checking the image displayed on the display unit 160. The display image is saved in a memory in the computer 150, a data management system connected to a modality by a network, or the like on the basis of a saving instruction from the user or the computer 150.

The computer 150 also performs driving control on the components included in the photoacoustic apparatus. The display unit 160 may also display a graphical user interface (GUI) or the like in addition to the image generated by the computer 150. The input unit 170 is configured such that the user can input information. The user can perform operations such as measurement start and end and the saving instruction of the generated image by using the input unit 170.

Hereinafter, details of the respective components of the photoacoustic apparatus according to the present exemplary embodiment will be described.

[Light Irradiation Unit 110]

The light irradiation unit 110 includes a light source 111 that emits light and an optical system 112 that guides the light emitted from the light source 111 to the object 100. It should be noted that the light includes pulse light such as a so-called rectangular wave or chopping wave.

A pulse width of the light emitted from the light source 111 may be a pulse width larger than or equal to 1 ns and smaller than or equal to 100 ns. A wavelength in a range between approximately 400 nm to approximately 1600 nm may be set as a wavelength of the light. A wavelength (which is higher than or equal to 400 nm and lower than or equal to 700 nm) at which absorption in the blood vessel is high may be used in a case where imaging of the blood vessel is performed at a high resolution. Light at a wavelength (which is higher than or equal to 700 nm and lower than or equal to 1100 nm) at which absorption in a background tissue (such as water or fat) of the living body is typically low may be used in a case where imaging of a deep part of the living body is performed.

A laser or a light emitting diode can be used as the light source 111. When measurement is performed by using light at a plurality of wavelengths, a light source that can change the wavelength may also be used. It should be noted that, in a case where the object is irradiated with the plurality of wavelengths, a plurality of light sources that generate light having mutually different wavelengths can be prepared, and the light is alternately emitted from the respective light sources. Even in a case where the plurality of light sources are used, those light sources are collectively represented as the light source. Various lasers including a solid-state laser, a gas laser, a dye laser, and a semiconductor laser can be used as the laser. For example, a pulse laser such as an Nd:YAG laser and an alexandrite laser may be used as the light source. In addition, a Ti:sa laser or an optical parametric oscillator (OPO) laser using Nd:YAG laser light as exciting light laser may be used as the light source. Moreover, a flash lamp or a light emitting diode may be used as the light source 111. Furthermore, a microwave source may be used as the light source 111.

An optical element such as a lens, a mirror, or an optical fiber can be used as the optical system 112. In a case where the breast or the like is set as the object 100, a light outgoing part of the optical system 112 may be constituted by a diffusing plate or the like that diffuses the light to perform the irradiation by widening a beam diameter of the pulse light. On the other hand, the light outgoing part of the optical system 112 may be constituted by a lens or the like, and the irradiation may be performed while the beam is focused in a photoacoustic microscope to increase the resolution.

It should be noted that the light irradiation unit 110 may directly irradiate the object 100 with light from the light source 111 without the provision of the optical system 112.

[Reception Unit 120]

The reception unit 120 includes transducers 121 that output an electric signal when the acoustic wave is received and a supporting member 122 that supports the transducers 121. A transmission unit that transmits an acoustic wave may be set as the transducer 121. A transducer serving as a reception unit and the transducer serving as the transmission unit may be a single (common) transducer or may also be separate components.

A piezo-ceramic material represented by lead zirconate titanate (PZT), a polymer piezoelectric membrane material represented by polyvinylidene-fluoride (PVDF), or the like can be used as a member constituting the transducer 121. An element other than a piezoelectric element may also be used. For example, a capacitive micro-machined ultrasonic transducer (CMUT), a transducer using a Fabry-Perot interferometer, or the like can be used. It should be noted that any transducer may be adopted as long as the transducer can output the electric signal when the acoustic wave is received. The signal obtained by the transducer is a time-resolved signal. That is, an amplitude of the signal obtained by the transducer represents a value based on a sound pressure received by the transducer at each time (for example, a value in proportion to the sound pressure).

A frequency component constituting the photoacoustic wave is typically 100 KHz to 100 MHz, and it is possible to adopt an element that can detect these frequencies as the transducer 121.

The supporting member 122 may be formed of a metallic material having a high mechanical strength or the like. A surface on a side of the object 100 of the supporting member 122 may be processed to have a mirror surface or realize light scattering such that much irradiation light enters the object. According to the present exemplary embodiment, the supporting member 122 has a shape of a hemispherical enclosure and is constituted such that the plurality of transducers 121 can be supported on the hemispherical enclosure. In this case, directional axes of the transducers 121 arranged in the supporting member 122 converge in the vicinity of the center of curvature of the hemispherical enclosure. An image quality in the vicinity of the center of curvature is increased when the imaging is performed by using the signals output from the plurality of transducers 121. It should be noted that the supporting member 122 may adopt any configuration as long as the supporting member 122 can support the transducers 121. The plurality of transducers may be disposed and arranged in a plane or a curved-surface such as a so-called 1D array, 1.5D array, 1.75D array, or 2D array in the supporting member 122. The plurality of transducers 121 are equivalent to a plurality of reception units.

The supporting member 122 may also function as a container that retains an acoustic matching material 210. That is, the supporting member 122 may be constituted by a container that arranges the acoustic matching material 210 between the transducer 121 and the object 100.

The reception unit 120 may include an amplifier that amplifies a time-series analog signal output from the transducer 121. The reception unit 120 may also include an analog-to-digital (A/D) converter that converts the time-series analog signal output from the transducer 121 into a time-series digital signal. That is, the reception unit 120 may include the signal collection unit 140 which will be described below.

It should be noted that the transducers 121 may be ideally arranged so as to surround the object 100 from the entire circumference such that the acoustic waves can be detected at various angles. It should be noted however that, in a case where the transducers are not arranged so as to surround the object 100 from the entire circumference because the object 100 is large, the transducers may be arranged on the hemispherical supporting member 122 to substantially establish a state in which the object 100 is surrounded from the entire circumference.

It should be noted that the arrangement and the number of the transducers and the shape of the supporting member may be optimized in accordance with the object, and any type of the reception unit 120 can be adopted with regard to the exemplary embodiment of the present invention.

A space between the reception unit 120 and the object 100 is filled with a medium with which the photoacoustic wave propagates. By using a material in which the acoustic wave can propagate, acoustic characteristics are matched on an interface between the object 100 and the transducer 121, and a material that allows transmittance of the photoacoustic wave as high as possible is adopted. For example, water, ultrasonic gel, or the like may be adopted as the material.

FIG. 4A is a lateral view of the probe 180, and FIG. 4B is a top view of the probe 180 (viewed from an upward direction along the plane of the paper in FIG. 4A). The probe 180 according to the present exemplary embodiment illustrated in FIGS. 4A and 4B includes the reception unit 120 in which the plurality of transducers 121 are three-dimensionally arranged in the hemispherical supporting member 122 having openings. The light outgoing part of the optical system 112 is arranged in a bottom part of the supporting member 122 in the probe 180 illustrated in FIGS. 4A and 4B.

According to the present exemplary embodiment, as illustrated in FIGS. 4A and 4B, a shape of the object 100 is maintained while the object 100 is in contact with a holding part 200. According to the present exemplary embodiment, in a case where the object 100 is a breast, a mode is presumed in which a bunk (or table) that supports an examinee in a prone position is provided with an opening for inserting the breast, and the breast suspended in a vertical direction through the opening is measured.

A space between the reception unit 120 and the holding part 200 is filled with a medium (the acoustic matching material 210) in which the photoacoustic wave can propagate. By using a material in which the acoustic wave can propagate, the acoustic characteristics are matched on the interface between the object 100 and the transducer 121, and a material that allows the transmittance of the photoacoustic wave as high as possible is adopted. For example, water, ultrasonic gel, or the like may be adopted as this medium.

The holding part 200 as a holding unit is used for holding the shape of the object 100 during the measurement. While the holding part 200 holds the object 100, a movement of the object 100 can be suppressed, and the position of the object 100 can be kept in the holding part 200. A resin material such as polycarbonate, polyethylene, or polyethylene terephthalate can be used as a material of the holding part 200.

The holding part 200 is preferably formed of a material having a firmness to such an extent that the object 100 can be held. The holding part 200 may be formed of a material through which the light used in the measurement transmits. The holding part 200 may be formed of a material in which an impedance is at a comparable level with that of the object 100. In a case where on object having a curvature of the breast or the like is set as the object 100, the holding part 200 molded to have a concave shape may also be adopted. In this case, the object 100 can be inserted into a concave part of the holding part 200.

The holding part 200 is attached to a fitting part 201. The fitting part 201 may be constituted in a manner that a plurality of types of the holding parts 200 can be replaced in accordance with the size of the object. For example, the fitting part 201 may also be constituted in a manner that holding parts having different radii of curvature, centers of curvature, or the like can be replaced.

A tag 202 in which information of the holding part 200 is registered may be installed in the holding part 200. For example, it is possible to register information such as the radius of curvature or the center of curvature of the holding part 200, acoustic velocity, or a discrimination ID in the tag 202. The information registered in the tag 202 is read out by a reading unit 203 to be transferred to the computer 150. To easily read the tag 202 when the holding part 200 is attached to the fitting part 201, the reading unit 203 may be installed in the fitting part 201. For example, the tag 202 is a barcode, and the reading unit 203 is a barcode reader.

[Driving Unit 130]

The driving unit 130 is a part that changes a relative position of the object 100 and the reception unit 120. According to the present exemplary embodiment, the driving unit 130 is an apparatus that moves the supporting member 122 in an XY direction and is an electrically-driven XY stage to which a stepping motor is mounted. The driving unit 130 includes a motor such as the stepping motor that generates driving force, a driving mechanism that transmits the driving force, and a positional sensor that detects positional information of the reception unit 120. A lead screw mechanism, a link mechanism, a gear mechanism, an oil pressure mechanism, or the like can be used as the driving mechanism. A potentiometer or the like using an encoder, a variable resistor, or the like can be used as the positional sensor.

It should be noted that the driving unit 130 may not only change the relative position of the object 100 and the reception unit 120 in the XY direction (two dimensions) but also change one-dimensionally or three-dimensionally. A movement path may be two-dimensionally scanned in a spiral shape or a line and space manner, and furthermore, the movement path may be three-dimensionally inclined along a body surface. In addition, the probe 180 may be moved so as to keep a constant distance from the surface of the object 100. At this time, the driving unit 130 may measure the movement amount of the probe by monitoring the number of revolutions of the motor or the like.

It should be noted that the driving unit 130 may fix the reception unit 120 and move the object 100 as long as the relative position of the object 100 and the reception unit 120 can be changed. A configuration in which the object 100 is moved by moving the holding part that holds the object 100 or the like is conceivable in a case where the object 100 is moved. Both the object 100 and the reception unit 120 may also be moved.

The driving unit 130 may continuously move the relative position or may move the relative position by a step and repeat manner. The driving unit 130 may be an electrically-driven stage that moves the relative position on a programmed track or a manually-operated stage. That is, the photoacoustic apparatus may be of a hand-held type in which the user performs the operation by holding the probe 180 without the provision of the driving unit 130.

In addition, according to the present exemplary embodiment, the driving unit 130 simultaneously drives the light irradiation unit 110 and the reception unit 120 to perform the scanning, but only the light irradiation unit 110 may be driven, and also only the reception unit 120 may be driven.

[Signal Collection Unit 140]

The signal collection unit 140 includes an amplifier that amplifies the electric signal corresponding to the analog signal output from the transducer 121, and an analog-to-digital (A/D) converter that converts the analog signal output from the amplifier into a digital signal. The signal collection unit 140 may be constituted by a field programmable gate array (FPGA) chip or the like. The digital signal output from the signal collection unit 140 is stored in the storage unit 152 in the computer 150. The signal collection unit 140 is also referred to as a data acquisition system (DAS). The electric signal in the present specification is a concept including both of the analog signal and the digital signal. It should be noted that the signal collection unit 140 may be connected to a light detection sensor attached to the light outgoing part of the light irradiation unit 110, and start processing in synchronism with the light emitted from the light irradiation unit 110 as a trigger. In addition, the signal collection unit 140 may start the processing in synchronism with an instruction issued by using a freeze button or the like as a trigger.

[Computer 150]

The computer 150 serving as a display control apparatus includes an arithmetic operation unit 151, a storage unit 152, and a control unit 153. Functions of the respective components will be described when a processing flow will be described.

Units realizing an arithmetic operation function as the arithmetic operation unit 151 can be constituted by a processor such as a CPU or a graphics processing unit (GPU) or an arithmetic operation circuit such as a field programmable gate array (FPGA) chip. These units may be constituted by not only a single processor or arithmetic operation circuit but also a plurality of processors or arithmetic operation circuits. The arithmetic operation unit 151 may receive various parameters such as the object acoustic velocity or the configuration of the holding part from the input unit 170 and process the reception signal.

The storage unit 152 can be constituted by a read only memory (ROM) or a non-transitory storage medium such as a magnetic disc or a flash memory. The storage unit 152 may also be a volatile medium such as a random access memory (RAM). It should be noted that the storage medium that stores the program is the non-transitory storage medium. It should also be noted that the storage unit 152 may be not only constituted by a single storage medium but also constituted by a plurality of storage media.

The storage unit 152 can save image data indicating the photoacoustic image generated by the arithmetic operation unit 151 by a method which will be described below.

The control unit 153 is constituted by an arithmetic operation element such as a CPU. The control unit 153 controls operations of the respective components of the photoacoustic apparatus. The control unit 153 may receive instruction signals based on various operations such as measurement start from the input unit 170, and control the respective components of the photoacoustic apparatus. The control unit 153 also reads out program codes stored in the storage unit 152 and controls actions of the respective components of the photoacoustic apparatus.

The computer 150 may be a dedicatedly designed work station. Respective components of the computer 150 may be constituted by different hardware components. In addition, at least part of the configurations of the computer 150 may be constituted by a single piece of hardware.

Figure 5:
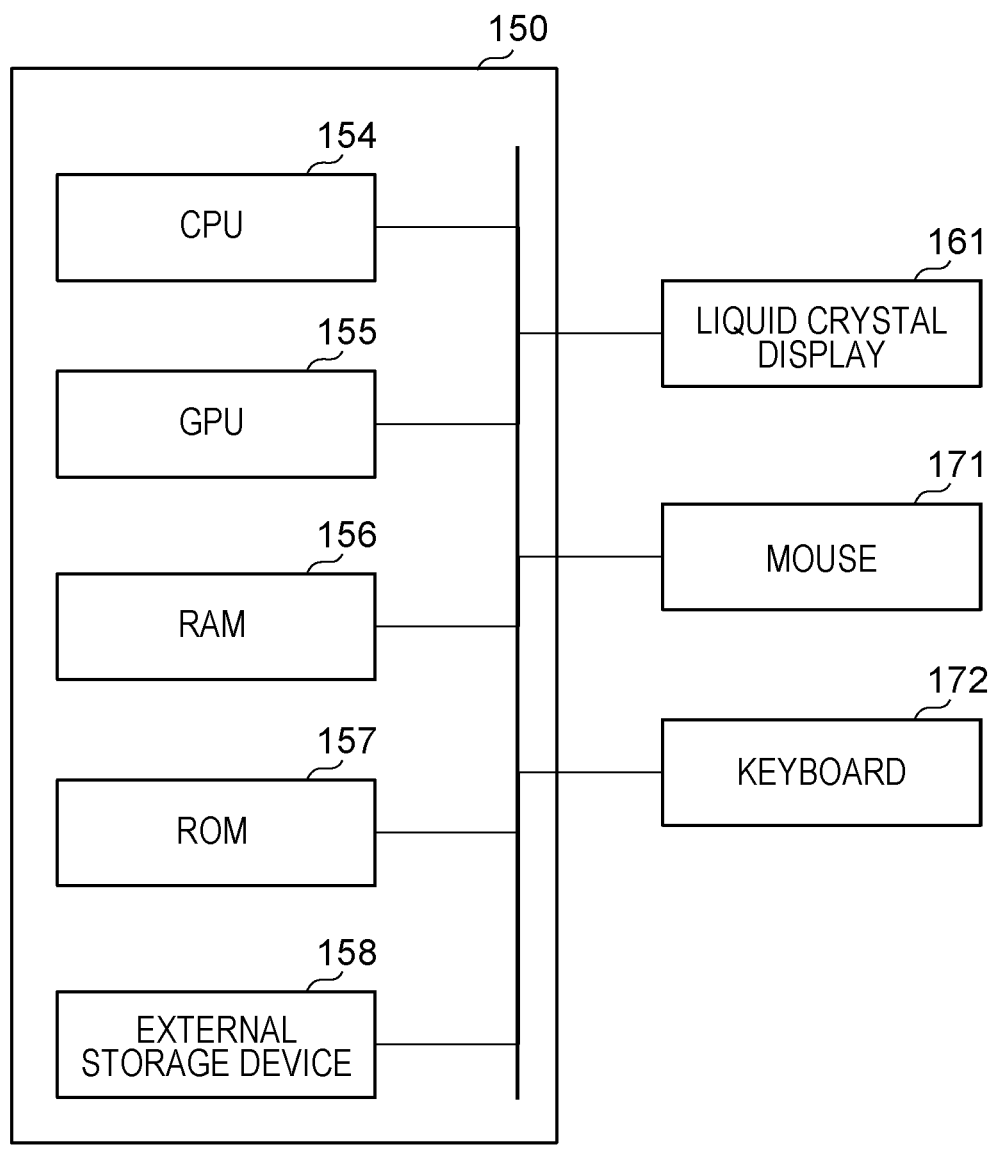
FIG. 5 is a block diagram illustrating a configuration of a computer and its surrounding according to the first exemplary embodiment.

FIG. 5 illustrates a specific configuration example of the computer 150 according to the present exemplary embodiment. The computer 150 according to the present exemplary embodiment is constituted by a CPU 154, a GPU 155, a RAM 156, a ROM 157, and an external storage device 158. A liquid crystal display 161 functioning as the display unit 160 and a mouse 171 and a keyboard 172 functioning as the input unit 170 are connected to the computer 150.

The computer 150 and the plurality of transducers 121 may be provided by a configuration of being contained in a common casing. It should be noted however that the computer contained in the casing may perform part of the signal processing, and a computer installed outside the casing may perform the rest of the signal processing. In this case, the computers installed inside and outside the casing can be collectively referred to as the computer according to the present exemplary embodiment. That is, it is sufficient even when hardware components constituting the computer are not contained in the single casing.

[Display Unit 160]

The display unit 160 is a display such as a liquid crystal display, an organic electro luminescence (EL) FED, a spectacle display, or a head mounted display. The display unit 160 is an apparatus that displays an image based on the object information or the like obtained by the computer 150, a numeric value of a specific position, or the like. The display unit 160 may display a GUI for operating the image or the apparatus. It should be noted that, when the object information is displayed, image processing (such as adjustment of the luminance value) may be performed in the display unit 160 or the computer 150 before the display is performed. The display unit 160 may be provided separately in addition to the photoacoustic apparatus. The computer 150 can transmit the photoacoustic image data to the display unit 160 in a wired or wireless manner.

[Input Unit 170]

An operation console can be adopted as the input unit 170. The operation console is constituted by a mouse, a keyboard, or the like that can be operated by the user. The display unit 160 may be constituted by a touch panel, and the display unit 160 can be used as the input unit 170.

The input unit 170 may be constituted such that information of a position or a depth to be desired to be observed or the like can be input. As an input method, a numeric value may be input, or an input operation can be performed by operating a slider bar. The image to be displayed on the display unit 160 may be updated in accordance with the input information. As a result, the user can set appropriate parameters by checking at the image generated by the parameters determined by its own operation.

It should be noted that the respective components of the photoacoustic apparatus may be constituted as individual apparatuses or may be constituted as an integrated single apparatus. A configuration as a single apparatus may also be adopted in which at least part of the components of the photoacoustic apparatus is integrated.

The information transmitted and received between the respective components of the photoacoustic apparatus is exchanged in a wired or wireless manner.

[Object 100]

The object 100 will be described below although the object 100 does not constitute the photoacoustic apparatus. The photoacoustic apparatus according to the present exemplary embodiment can be used for a purpose of a diagnosis on malignant tumor, blood vessel disease, or the like of a human being or an animal, follow-up of a chemical treatment, or the like. Therefore, a living body, specifically, a target region of the diagnosis such as a human or animal breast, respective organs, a network of vessels, a head region, a neck region, an abdominal region, or four limbs including fingers and toes is presumed as the object 100. For example, when a human body is the measurement object, a newborn blood vessel formed in the vicinity of a blood vessel or tumor containing a large amount of oxyhemoglobin or deoxyhemoglobin or the like may be set as the target of the optical absorber. Plaque of a carotid wall or the like may also be set as the target of the optical absorber. In addition, pigment such as methylene blue (MB) or indocyanine green (ICG), fine gold particles, or a material where those materials are accumulated or a chemically modified material introduced from the outside may be set as the optical absorber.

Next, a display method including information processing according to the present exemplary embodiment will be described with reference to FIG. 6. It should be noted that respective steps are executed while the computer 150 controls the operations of the components of the photoacoustic apparatus.

<S100: Step of Setting Control Parameter>

The user uses the input unit 170 to specify a control parameter such as an irradiation condition (repetition frequency or wavelength) of the light irradiation unit 110 which is used for obtaining the object information or a position of the probe 180. The computer 150 sets the control parameter determined on the basis of the instruction of the user.

<S200: Step of Moving Probe to Specified Position>

The control unit 153 causes the driving unit 130 to move the probe 180 to a specified position on the basis of the control parameter specified in step S100. In a case where the imaging is specified in a plurality of positions in step S100, first, the driving unit 130 moves the probe 180 to an initial specified position. It should be noted that the driving unit 130 may move the probe 180 to a previously programmed position when a start instruction for measurement is issued. It should also be noted that the user may hold the probe 180 to be moved to a desired position in a case where the photoacoustic apparatus is of the hand-held type.

<S300: Step of Performing Light Irradiation>

The light irradiation unit 110 irradiates the object 100 with light on the basis of the control parameter specified in Step S100.

The object 100 is irradiated with the light generated from the light source 111 via the optical system 112 as the pulse light. Subsequently, the pulse light is absorbed inside the object 100, and the photoacoustic wave is generated by the photoacoustic effect. The light irradiation unit 110 transmits a synchronization signal to the signal collection unit 140 along with the transmission of the pulse light.

<S400: Step of Receiving Photoacoustic Wave>

The signal collection unit 140 starts signal collection when the synchronization signal transmitted from the light irradiation unit 110 is received. That is, the signal collection unit 140 performs amplification and AD conversion of the analog electric signal derived from the acoustic wave which is output from the reception unit 120 to generate the amplified digital electric signal to be output to the computer 150. The computer 150 saves the signal transmitted from the signal collection unit 140 in the storage unit 152. In a case where the imaging is specified in a plurality of scanning positions in step S100, steps S200 to S400 are repeatedly executed in the specified scanning positions, and the pulse light irradiation and the generation of the digital signal derived from the acoustic wave are repeated.

<S500: Step of Generating Photoacoustic Image Data>

The arithmetic operation unit 151 in the computer 150 generates the photoacoustic image data as the volume data based on signal data stored in the storage unit 152 and saves the photoacoustic image data in the storage unit 152. Any techniques such as a time domain reverse projection method, a Fourier domain reverse projection method, or a model base method (repeated operation method) may be adopted as a reconstruction algorithm for converting the signal data into the three-dimensional volume data. For example, the time domain reverse projection method includes universal back-projection (UBP), filtered back-projection (FBP), phasing addition (delay-and-sum), or the like. For example, the arithmetic operation unit 151 may adopt a UBP method represented by Expression (1) as the reconstruction technology for obtaining a three-dimensional spatial distribution of a generated sound pressure (initial sound pressure) of the acoustic wave as the photoacoustic image data

[Math. 1]

$$p_0(r_0) = \frac{\sum_{i}^{N} b\left(r_i, t = \frac{|r_i - r_0|}{c}\right) \cdot \Delta\Omega_i}{\sum_{i}^{N} \Delta\Omega_i} \quad (1)$$

$$b(r, t) = 2p(r, t) - 2t\frac{\partial p(r, t)}{\partial t}$$

Where $r_0$ denotes a positional vector indicating a position for performing reconstruction (also referred to as a reconstruction position or a position of interest), $p_0(r_0, t)$ denotes an initial sound pressure in the position for performing the reconstruction, and c denotes the acoustic velocity of a propagation path. $\Delta\Omega_i$ denotes a solid angle viewing the i-th transducer 121 from the position for performing the reconstruction, and N denotes the number of transducers 121 used for the reconstruction. Expression (1) represents performance of phasing addition (reverse projection) by carrying out processing such as differentiation on reception signals p $(r_i, t)$ and applying weighting of the solid angle to those. Herein, t in Expression (1) denotes a time (propagation time) for the photoacoustic wave to propagate through an acoustic ray between the position of interest and the transducer 121. It should be noted that arithmetic operation processing may also be performed in a calculation of b $(r_i, t)$. For example, the arithmetic operation processing includes frequency filtering (low-pass, high-pass, band-pass, or the like), deconvolution, envelope demodulation, wavelet filtering, or the like.

The arithmetic operation unit 151 may also obtain absorption coefficient distribution information by calculating the light fluence distribution inside the object 100 of the light with which the object 100 is irradiated and dividing an initial sound pressure distribution by the light fluence distribution. In this case, the absorption coefficient distribution information may be obtained as the photoacoustic image data. The computer 150 can calculate a spatial distribution of the light fluence inside the object 100 by a method of numerically solving a transport equation or a diffusion equation representing a behavior of light energy in a medium that absorbs or diffuses light. A finite element method, a difference method, a Monte Carlo method, or the like can be adopted as a numerically solving method. For example, the computer 150 may calculate the spatial distribution of the light fluence inside the object 100 by solving a light diffusion equation represented by Expression (2).

[Math. 2]

$$\frac{1}{c}\frac{\partial}{\partial t}\Phi(r, t) = -\mu_a \Phi(r, t) + \nabla \cdot (D\nabla\Phi(r, t)) + S(r, t) \quad (2)$$

Where D denotes a diffusion coefficient, $\mu_a$ denotes an absorption coefficient, S denotes an incidence intensity of the irradiation light, $\varphi$ denotes a reaching light fluence, r denotes a position, and t denotes time.

In addition, steps S300 and S400 may be executed by using light at a plurality of wavelengths, and the arithmetic operation unit 151 may obtain the absorption coefficient distribution information corresponding to each of the light at the plurality of wavelengths. The arithmetic operation unit 151 may obtain spatial distribution information of a concentration of a material constituting the object 100 as spectroscopic information as the photoacoustic image data on the basis of the absorption coefficient distribution information corresponding to each of the light at the plurality of wavelengths. That is, the arithmetic operation unit 151 may obtain spectroscopic information by using signal data corresponding to the light at the plurality of wavelengths.

<S600: Step of Generating and Displaying Parallel Image Based on Photoacoustic Image Data>

The computer 150 serving as the display control unit generates an image on the basis of the photoacoustic image data obtained in S500 and causes the display unit 160 to display the image. According to the present exemplary embodiment, the computer 150 generates the first photoacoustic image corresponding to the first spatial region on the basis of the photoacoustic image data. The computer 150 generates the first photoacoustic image representing the photoacoustic image data corresponding to the first spatial region by performing rendering of the photoacoustic image data corresponding to the first spatial region. The computer 150 also generates the second photoacoustic image corresponding to the second spatial region having a different thickness in the viewing direction of the rendering from that of the first spatial region and a spatial region superimposed with the first spatial region on the basis of the photoacoustic image data. The computer 150 generates the second photoacoustic image representing the photoacoustic image data corresponding to the second spatial region by performing rendering of the photoacoustic image data corresponding to the second spatial region. Subsequently, the computer 150 generates a parallel image in which the first photoacoustic image and the second photoacoustic image are arranged side by side and transmits the parallel image to the display unit 160. The computer 150 causes the display unit 160 to display the parallel image.

Figure 7A:
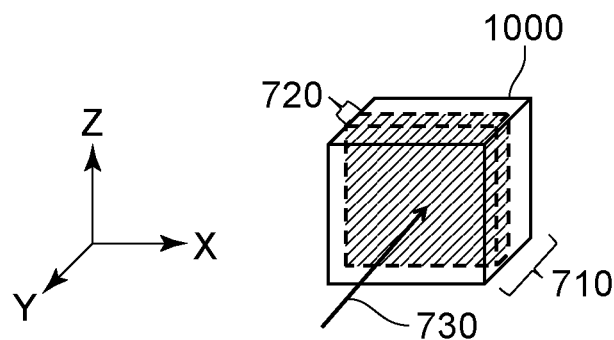
FIG. 7A is a schematic diagram illustrating the image display method according to the first exemplary embodiment.

For example, as illustrated in FIG. 7A, the computer 150 sets an entire region of the photoacoustic image data 1000 as the first spatial region 710 and sets a partial region of the photoacoustic image data 1000 as the second spatial region 720.

Figure 7B:
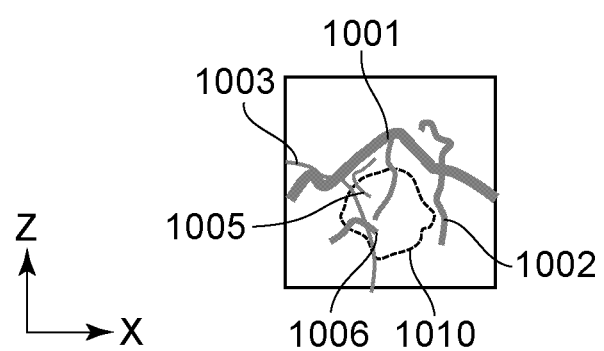
FIG. 7B is a schematic diagram illustrating the image display method according to the first exemplary embodiment.
Figure 7C:
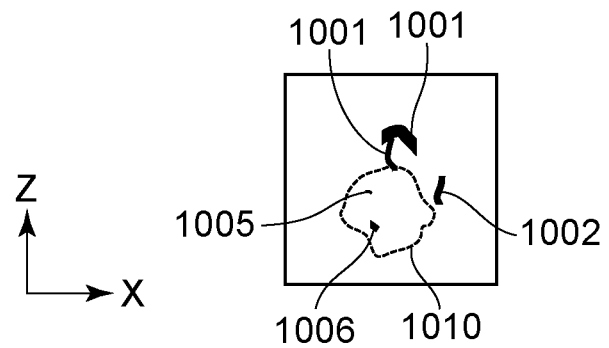
FIG. 7C is a schematic diagram illustrating the image display method according to the first exemplary embodiment.

The computer 150 generates an MIP image 740 (first photoacoustic image) by performing the maximum intensity projection of the photoacoustic image data 1000 corresponding to the first spatial region 710 illustrated in FIG. 7A in a viewing direction 730 (Y-axis direction) (FIG. 7B). The computer 150 also generates an MIP image 750 (second photoacoustic image) by performing the maximum intensity projection of the photoacoustic image data 1000 corresponding to the second spatial region 720 in the viewing direction 730 (FIG. 7C). The thus obtained MIP images are photoacoustic images respectively corresponding to the first spatial region and the second spatial region. It should be noted that a schematic diagram corresponding to the tumor 1010 existing in the second spatial region 720 is illustrated in both FIG. 7B and FIG. 7C for convenience although this is not the image data included in photoacoustic image data 1000.

The computer 150 generates an image obtained in which the MIP image 740 illustrated in FIG. 7B and the MIP image 750 illustrated in FIG. 7C are arranged side by side and causes the display unit 160 to display the image. When the photoacoustic image data is displayed in the above-described manner, it is possible to understand the continuous structure of the blood vessel on the basis of the MIP image 740, and it is also possible to understand the local structure and a detailed position of the blood vessel at the same time on the basis of the MIP image 750. In addition, when the image corresponding to the tumor 1010 existing in the second spatial region 720 is superimposed on the respective MIP images, while the blood vessel thought to be intruding into the tumor is identified on the basis of the MIP image 740 representing the continuous blood vessel structure, it is possible to confirm that the blood vessel is intruding into the tumor on the basis of MIP image 750 representing the local blood vessel structure. According to the present exemplary embodiment, since the same blood vessel is set as a display object in the respective images, when the respective images are generated by the same technique (maximum intensity projection method), it is facilitated to understand the structures commonly represented in the respective images.

It should be noted that the first spatial region 710 is set as the entire region of the photoacoustic image data 1000 in the example illustrated in FIGS. 7A to 7F, but a partial region of the photoacoustic image data 1000 may be set as the first spatial region 710.

In addition, the second spatial region 720 is a partial spatial region of the first spatial region 710 in the example illustrated in FIGS. 7A to 7F, but it is sufficient when the second spatial region 720 has a different thickness in the viewing direction of the rendering from that of the first spatial region 710 and also has a superimposed spatial region. In this case too, since the same structure can be understood in the MIP image 740 and the MIP image 750, it is facilitated to understand the structure of the blood vessel. It should be noted that a thickness in the viewing direction of the rendering of the second spatial region 720 is preferably set to be smaller than that of the first spatial region 710. With this configuration, the entire structure and the local structure of the imaging object can be understood at the same time.

Moreover, the maximum intensity projection of the photoacoustic image data of the spatial region desired to be imaged is performed in the example illustrated in FIGS. 7A to 7F, but any technique may be used to perform the imaging (rendering) as long as the method include displaying an image that can represent the photoacoustic image data of the spatial region desired to be imaged. For example, rendering may be performed in a manner that opacity of the photoacoustic image data of the spatial region except for the first spatial region 710 is set as 0, and opacity is provided to the photoacoustic image data of the first spatial region 710. In addition, selective rendering of the photoacoustic image data of the first spatial region 710 may be performed by excluding the photoacoustic image data of the spatial region except for the first spatial region from the rendering target. It should be noted that any techniques in related art such as the maximum intensity projection method (MIP), minimum intensity projection (MinIP), Ray Sum, mean value projection, and median value projection, volume rendering, and surface rendering may be adopted for the rendering. The rendering technique may be roughly classified into the surface rendering and the volume rendering, and it may be defined that the maximum intensity projection method (MIP), minimum intensity projection (MinIP), Ray Sum, mean value projection, and median value projection are included in the volume rendering.

It should be noted that the imaging for representing the respective spatial regions may be performed by rendering of the same type. Rendering operations using different parameters or different pre-processings at the time of the rendering while algorithms of the rendering are the same are also included in the rendering of the same type. In addition, with regard to the rendering in accordance with the spatial regions for the imaging for representing the respective spatial regions, for example, the image corresponding to the first spatial region may be generated by the volume rendering to be displayed, and the image corresponding to the second spatial region may be generated by the MIP to be displayed. It should be noted that the photoacoustic apparatus according to the present exemplary embodiment may be structured such that the user can select the rendering technique by using the input unit 170. In a case where an array direction of reconstructed voxels and the viewing direction (projection direction) are not matched with each other, the reconstructed voxels may be divided, and rendering processing may be executed with respect to the interpolated volume data. The example of a parallel projection method has in which the viewing direction is one direction been described above, but an image may be generated by a perspective projection method by projecting directions extending in a radial manner from a certain point onto the viewing direction (projection direction) to be displayed.

The position, the range, or the like of at least one of the first spatial region 710 and the second spatial region 720 may also be changed to update the image into a parallel image corresponding to the changed spatial region to be displayed. It should be noted that the change of the spatial region may be performed by an instruction by the user using the input unit 170 or performed when the computer 150 updates the display image while the spatial region is changed by a predetermined pattern. When the spatial region desired to be imaged is changed in the above-described manner, and the switching to the image corresponding to the changed spatial region is performed to be displayed, and the images can be sequentially fed and displayed.

Figure 7D:
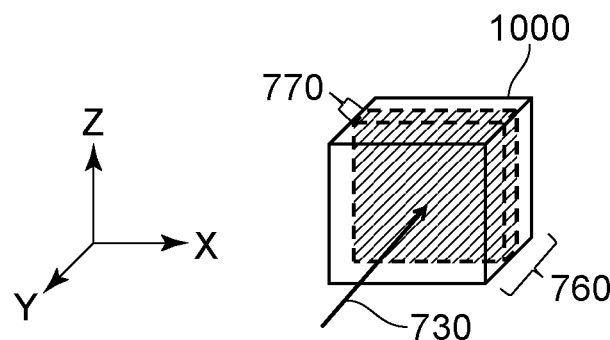
FIG. 7D is a schematic diagram illustrating the image display method according to the first exemplary embodiment.
Figure 7E:
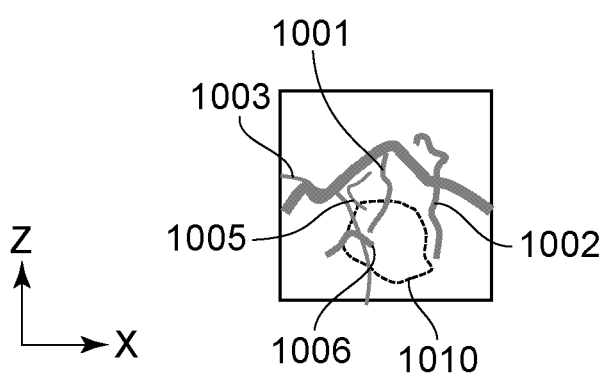
FIG. 7E is a schematic diagram illustrating the image display method according to the first exemplary embodiment.
Figure 7F:
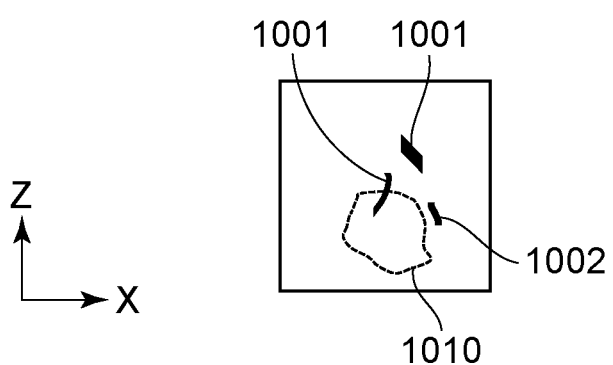
FIG. 7F is a schematic diagram illustrating the image display method according to the first exemplary embodiment.

For example, a case will be described where the user operates a wheel of a mouse serving as the input unit 170 to issue an instruction for changing the spatial region desired to be represented as the image, and the display images are sequentially switched. First, the computer 150 accepts operation instruction information from the user, and the setting of a second spatial region 770 is changed from the second spatial region 720 illustrated in FIG. 7A to the partial spatial region of the photoacoustic image data 1000 as illustrated in FIG. 7D. Herein, the description will be provided while the user does not issue an instruction for changing the first spatial region. That is, the first spatial region 710 illustrated in FIG. 7A and a first spatial region 760 illustrated in FIG. 7D are the same spatial region, but the second spatial region 720 illustrated in FIG. 7A and the second spatial region 770 illustrated in FIG. 7D are different spatial regions.

The computer 150 generates an MIP image 780 (first photoacoustic image) by performing the maximum intensity projection of the photoacoustic image data 1000 of the first spatial region 760 illustrated in FIG. 7D in the viewing direction 730 (Y-axis direction). The computer 150 also generates an MIP image 790 (second photoacoustic image) by performing the maximum intensity projection of the photoacoustic image data 1000 of the second spatial region 770 in the viewing direction 730. The thus obtained respective MIP images are the photoacoustic images corresponding to the first spatial region and the second spatial region which have been respectively set again.

The computer 150 generates images in which the respective MIP images corresponding to the respective changed spatial regions are arranged side by side and causes the display unit 160 to display the images. In this manner, the parallel images corresponding to the different spatial regions can be sequentially switched and displayed.

FIG. 8 is a conceptual diagram for describing the generation of the parallel images corresponding to the above-described plurality of spatial regions. That is, FIG. 8 is a conceptual diagram at a time when an entire MIP image in which an entire region of photoacoustic image data 800 is set as the first spatial region and a partial MIP image (slice image) in which a partial region of the photoacoustic image data 800 is set as the second spatial region are arranged side by side to generate the parallel image as described above.

The computer 150 generates an entire MIP image 810 by performing the maximum intensity projection (entire MIP) of the entire region of the photoacoustic image data 800 in the Y-axis direction as a projection object. The computer 150 also generates partial MIP images 821, 822, and 823 (slice images) by performing the maximum intensity projection (partial MIP) of each of the plurality of mutually different spatial regions corresponding to partial regions of the photoacoustic image data 800 in the Y-axis direction as the projection object.

For convenience, the example has been described in FIG. 8 in which the three partial MIP images are generated and three parallel images are generated, but four or more partial MIP images and four or more parallel images may also be generated.

It should be noted that the example in which the first spatial region is fixed has been described so far, but the first spatial region may be changed. For example, in a case where the first spatial region is a partial region of the photoacoustic image data, the position of the first spatial region and the position of the second spatial region may be changed in synchronism with each other on the basis of an instruction of the user or a predetermined switching pattern. That is, the first spatial region and the second spatial region may be moved manually or automatically by the same movement amount. When the positions of the spatial regions are changed in the above-described manner, since a positional relationship between imaging regions of the respective images that are set as display targets is maintained, there is little sense of discomfort at the time of the switching of the display image.

Figure 9A:
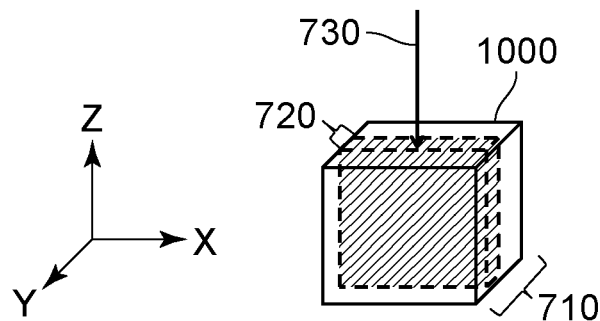
FIG. 9A is a schematic diagram illustrating the image display method from another viewing direction according to the first exemplary embodiment.
Figure 9B:
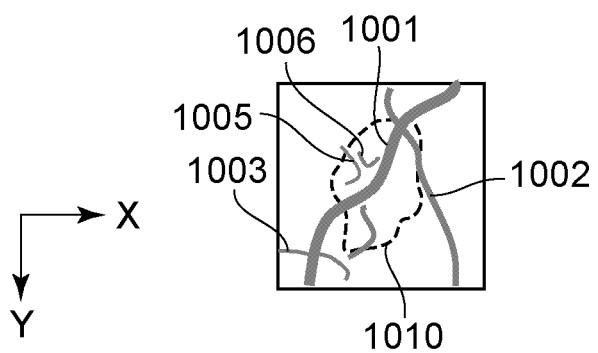
FIG. 9B is a schematic diagram illustrating the image display method from the other viewing direction according to the first exemplary embodiment.
Figure 9C:
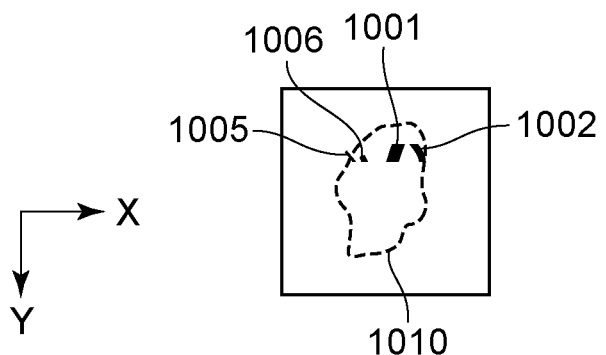
FIG. 9C is a schematic diagram illustrating the image display method from the other viewing direction according to the first exemplary embodiment.

The viewing direction 730 can also be changed. The computer 150 may change the viewing direction 730 to display an image representing the photoacoustic image data observed from the changed viewing direction 730. The change of the viewing direction 730 may be performed by an instruction of the user using the input unit 170, or the display image may be updated while the computer 150 changes the viewing direction 730 by a predetermined pattern. For example, the user may instruct to change the viewing direction 730 to the Z-axis direction by using the input unit 170 as illustrated in FIG. 9A, and the computer 150 may generate the parallel image in accordance with the change instruction to update (or switch) the display image as illustrated in FIG. 9B. It should be noted that the computer 150 may generate parallel images corresponding to a plurality of viewing directions and cause the display unit 160 to display the parallel images side by side.

In addition, the display of the parallel image according to the present exemplary embodiment and the display of the superimposed image of the first photoacoustic image and the second photoacoustic image may be switched to perform the display or may be displayed side by side in accordance with the instruction of the user.

Moreover, a parallel image may be generated by arranging the photoacoustic image generated according to the present exemplary embodiment and a modality image representing volume data obtained by another modality other than the photoacoustic apparatus side by side. The volume data obtained by the modality such as the ultrasonic diagnosis apparatus, the MRI apparatus, the X-ray CT apparatus, or the PET apparatus can be adopted as the volume data obtained by the other modality. For example, the first photoacoustic image corresponding to the first spatial region is displayed in a first second display region of the display unit 160. In addition, the second photoacoustic image corresponding to the second spatial region is displayed in a second display region different from the first display region of the display unit 160. Furthermore, an MRI image representing the volume data obtained by the MRI apparatus may be displayed in a third display region different from the first display region and the second display region of the display unit 160.

Figure 10:
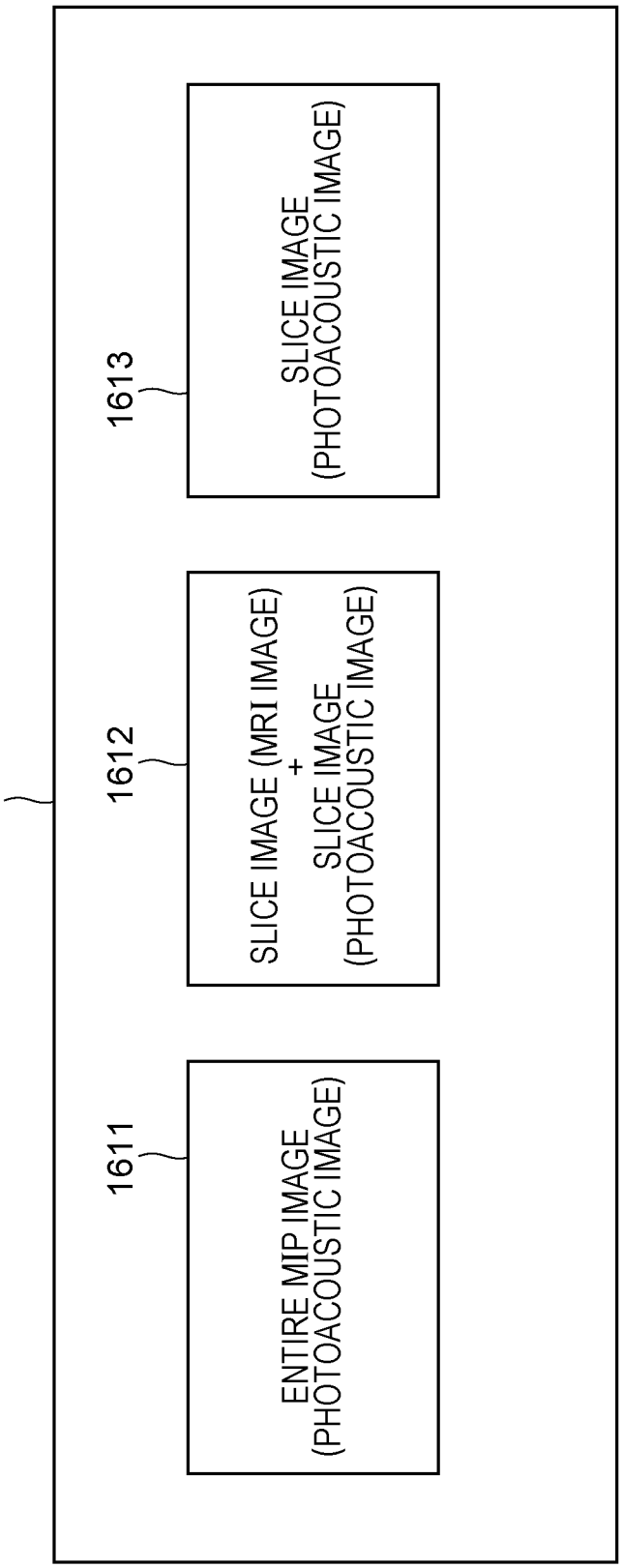
FIG. 10 is a schematic diagram illustrating an example of parallel display according to the first exemplary embodiment.

In addition, as illustrated in FIG. 10, the parallel image in which three or more images are arranged side by side may be displayed. For example, the entire MIP image (first photoacoustic image) of the photoacoustic image data is displayed in a first display region 1611 of the display unit 160. The superimposed image of the slice image (second photoacoustic image) of the photoacoustic image data and the slice image of the volume data of the other modality is displayed in a second display region 1612 of the display unit 160. Furthermore, the slice image (second photoacoustic image) of the photoacoustic image data may be displayed in a third display region 1613 of the display unit 160. In FIG. 10, the photoacoustic image as the slice image representing the photoacoustic image data corresponding to the second spatial region and the MRI image as the slice image representing the spatial region corresponding to the second spatial region are superimposed on each other to be displayed in the second display region 1612 of the display unit 160. In a case where a diagnosis is performed while the superimposed image by a multi-modality is set as a reference, when each of the first photoacoustic image and the second photoacoustic image is individually displayed so as to be adjacent to the superimposed image set as the reference, the reference by the doctor is facilitated at the time of the diagnosis. It should be noted that the computer 150 may set the MRI image (slice image) generated by the MRI apparatus as the base image and superimpose the photoacoustic image (slice image) obtained by the photoacoustic apparatus on the MRI image to display the superimposed image in the second display region 1612. When pieces of the information obtained by the plurality of modalities in the above-described manner are displayed at the same time, since pieces of the information such as the position of the blood vessel and the position of the tumor can be understood at the same time, it is possible to perform a comprehensive diagnosis.

It should be noted that the spatial regions corresponding to the second spatial regions in the respective modalities are preferably the same spatial region as the second spatial region. However, it may be difficult to extract the same spatial region in some cases due to a reason that voxel sizes vary among data or the like. For this reason, when the spatial region corresponding to the second spatial region is imaged, the spatial region corresponding to the second spatial region may be different from the second spatial region to such an extent that it is possible to visually recognize the representation of the second spatial region. For example, a case will be considered where the voxel size of the photoacoustic image data is 1 mm, and the voxel size of the MRI image data is 2 mm. In this case, when a slab having a thickness of 1 mm is set as the second spatial region with regard to the photoacoustic image, a slab having a thickness of 2 mm including this slab may be set as the spatial region corresponding to the second spatial region with regard to the MRI image.

It should be noted that the image display method based on the photoacoustic image data corresponding to the volume data derived from the photoacoustic wave has been described according to the present exemplary embodiment, but the image display method according to the present exemplary embodiment can also be applied to the volume data obtained by a modality other than the photoacoustic apparatus. The image display method according to the present exemplary embodiment may also be applied to the volume data obtained by the modality such as the ultrasonic diagnosis apparatus, the MRI apparatus, the X-ray CT apparatus, or the PET apparatus. In particular, the image display method according to the present exemplary embodiment can be preferably applied to the volume data including the image data representing the blood vessel. Since the blood vessel has a complex structure, how the blood vessel travels beyond there is not presumed in the tomographic image. When the large spatial region is projected, it is difficult to understand an anteroposterior relationship of the complex blood vessel. For this reason, the image display method according to the present exemplary embodiment can be preferably applied to the volume data including the image data representing the blood vessel. For example, at least one of the photoacoustic image data, MR blood vessel imaging method (MRA) image data, X-ray CT blood vessel imaging method (CTA) image data, and the Doppler image data can be adopted as the volume data including the image data representing the blood vessel.

The computer 150 may receive the volume data from the storage unit 152 and determine whether or not the image display method according to the present exemplary embodiment is used on the basis of information indicating an image type associated with the volume data. In a case where it is determined that the image type associated with the volume data is one of the photoacoustic image data, the MRA image data, the CTA image data, and the Doppler image data, the computer 150 may execute a method of displaying the parallel image according to the present exemplary embodiment.

It should be noted that the computer 150 may perform blood vessel extraction processing on the photoacoustic image data and display the photoacoustic image data on which the blood vessel extraction processing has been performed on the basis of the image display method according to the present exemplary embodiment.

According to the present exemplary embodiment, the example has been described in which the photoacoustic apparatus serving as the modality generates the volume data and executes the image display method according to the present exemplary embodiment with respect to the generated volume data. It should be noted however that the display control apparatus corresponding to a different apparatus from the modality may execute the image display method according to the present exemplary embodiment. In this case, the display control apparatus reads out and obtains the volume data previously generated by the modality from a storage unit such as a picture archiving and communication system (PACS) and applies the image display method according to the present exemplary embodiment to this volume data. In this manner, the image display method according to the exemplary embodiment of the present invention can also be applied to the previously generated volume data.

Second Exemplary Embodiment

According to a second exemplary embodiment, a mode will be described where an image based on volume data obtained by a different modality from the photoacoustic apparatus is superimposed and displayed in addition to the photoacoustic image described according to the first exemplary embodiment. In particular, an example of a case where the ultrasonic diagnosis apparatus is adopted as the different modality from the photoacoustic apparatus will be described according to the second exemplary embodiment. According to the second exemplary embodiment too, an apparatus similar to the photoacoustic apparatus described according to the first exemplary embodiment is used. The already described component will be assigned with the same reference sign, and a detailed description thereof will be omitted.

According to the present exemplary embodiment, when the transducer 121 of the probe 180 transmits an ultrasonic wave on the basis of a control signal from the control unit 153 and receives a reflection wave of the transmitted ultrasonic wave, an electric signal (also referred to as an ultrasonic signal) is output. It should be noted that a transducer configured to receive the ultrasonic wave and a transducer configured to receive the acoustic wave may be separately prepared. The transducer configured to receive the ultrasonic wave and the transducer configured to receive the acoustic wave may also be constructed by the same transducer. In addition, a transducer configured to transmit and receive the ultrasonic wave and a transducer configured to receive the photoacoustic wave may be separately prepared. The transducer configured to transmit and receive the ultrasonic wave and the transducer configured to receive the photoacoustic wave may also be constructed by the same transducer.

Figure 11:
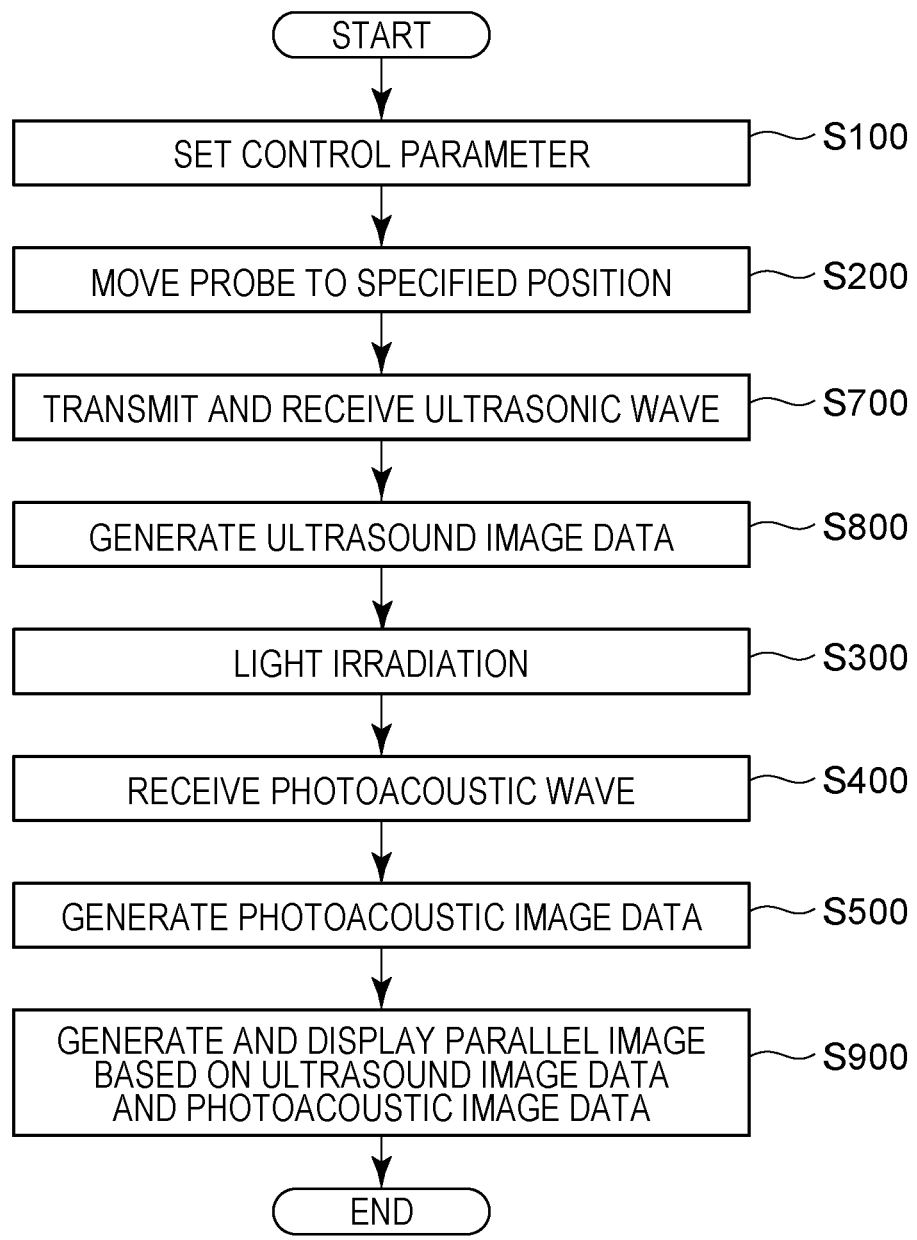
FIG. 11 is a flow chart of the image display method according to a second exemplary embodiment.

An image display method including information processing according to the present exemplary embodiment will be described with reference to FIG. 11. It should be noted that the respective steps are executed while the computer 150 controls the operations of the components of the photoacoustic apparatus. In addition, a step similar to the step illustrated in FIG. 6 will be assigned with the same reference sign, and a detailed description thereof will be omitted.

First, S100 and S200 are executed to move the probe 180 to a specified position.

<S700: Step of Transmitting and Receiving Ultrasonic Wave>

The probe 180 transmits and receives the ultrasonic wave with respect to the object 100 and outputs the ultrasonic signal. The signal collection unit 140 performs the A/D conversion processing or the like with respect to the ultrasonic signal and transmits the ultrasonic signal after the processing to the computer 150. The ultrasonic signal as the digital signal is stored in the storage unit 152.

It should be noted that, to generate three-dimensional ultrasound image data in S800 which will be described below, the probe 180 may collect ultrasonic signals by transmitting and receiving plane-wave ultrasonic waves in a plurality of directions. In addition, in a case where transmission and reception in a plurality of positions are to be performed to generate the three-dimensional ultrasound image data, the probe 180 may collects the ultrasonic signals by repeating the transmission and reception in the plurality of positions while the steps in S200 and S700 are repeatedly executed.

<S800: Step of Generating Ultrasound Image Data>

The arithmetic operation unit 151 generates the ultrasound image data corresponding to the three-dimensional volume data by performing reconstruction processing such as delay and sum with respect to the ultrasonic signals. Once the ultrasound image data is generated, the ultrasonic signals saved in the storage unit 152 may be deleted. According to the present exemplary embodiment, a case will be described where B mode image data is generated as the ultrasound image data. The B mode image data is the image data derived from the ultrasonic waves (echo) reflected by a boundary between different tissues and includes the image data representing the tumor or the like.

It should be noted that this step may be executed after all the ultrasonic signals are collected or this step may also be executed each time the transmission and reception of the ultrasonic wave are performed. Any method may be adopted in S700 and S800 as long as the three-dimensional ultrasound image data can be generated by the transmission and reception of the ultrasonic waves.

According to the present exemplary embodiment, the ultrasound image data of the spatial region similar to the photoacoustic image data generated in S500 is generated. It should be noted however that generation regions of the respective image data do not need to be completely the same as long as the photoacoustic image data and the ultrasound image data of the spatial region desired to be observed can be generated.

Subsequently, the probe 180 performs the light irradiation and the reception of the photoacoustic wave (S300 and S400), the computer 150 generates the photoacoustic image data of the spatial region the same as the ultrasound image data on the basis of the reception signal of the photoacoustic wave (S500). In a case where the light irradiation and the reception of the photoacoustic wave are performed plural times, the transmission and reception of the ultrasonic wave in S700 may be performed between one light irradiation and the next light irradiation. In addition, the generation of the ultrasound image data (S800) may be performed after the generation of the photoacoustic image data (S500).

<S900: Step of Generating and Displaying Superimposed Image Based on Ultrasound Image Data and Photoacoustic Image Data>

The computer 150 serving as the display control unit generates an image on the basis of the ultrasound image data obtained in S800 and the photoacoustic image data obtained in S500 and causes the display unit 160 to display the image. According to the present exemplary embodiment, the computer 150 generates the first photoacoustic image corresponding to the first spatial region on the basis of the photoacoustic image data. The computer 150 also generates the second photoacoustic image corresponding to the second spatial region having a different thickness in the viewing direction of the rendering from a thickness of the first spatial region and also including the spatial region superimposed with the first spatial region on the basis of the photoacoustic image data. Furthermore, the computer 150 generates an ultrasound image (B mode image) corresponding to the second spatial region on the basis of the ultrasound image data. This ultrasound image is an image representing the ultrasound image data corresponding to the second spatial region.

Subsequently, the computer 150 generates a superimposed image (first superimposed image) in which the first photoacoustic image and the ultrasound image are superimposed on each other. In addition, the computer 150 generates a superimposed image (second superimposed image) in which the second photoacoustic image and the ultrasound image are superimposed on each other. The computer 150 generates a parallel image in which the thus generated two superimposed images (first and second superimposed images) are arranged side by side and causes the display unit 160 to display the parallel image.

Figure 12A:
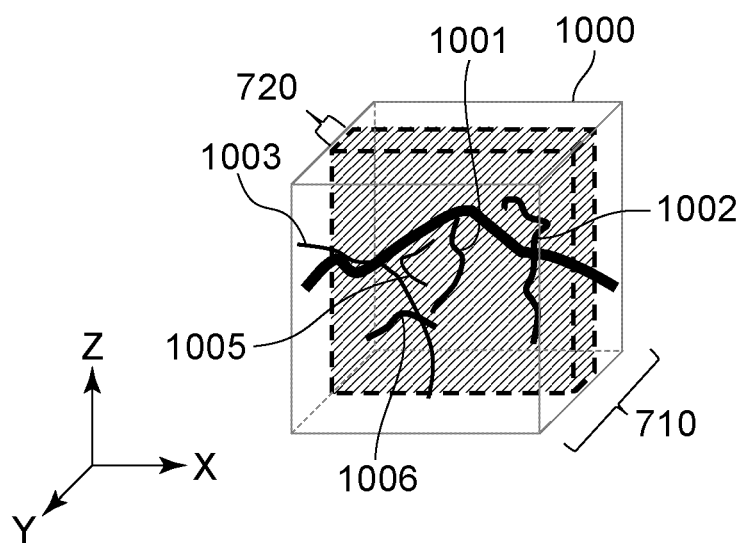
FIG. 12A is a schematic diagram illustrating the image display method according to the second exemplary embodiment.

For example, as illustrated in FIG. 12A, the computer 150 sets the entire region of the photoacoustic image data 1000 as the first spatial region 710 and sets the partial region of the photoacoustic image data 1000 as the second spatial region 720.

Figure 12B:
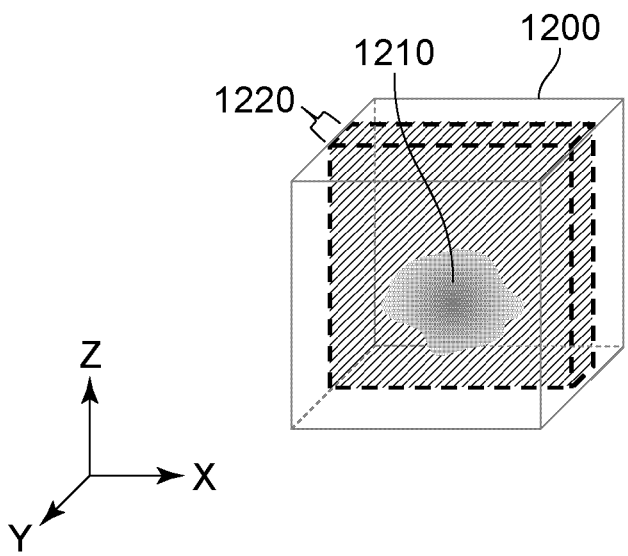
FIG. 12B is a schematic diagram illustrating the image display method according to the second exemplary embodiment.

In addition, according to the present exemplary embodiment, as illustrated in FIG. 12B, the computer 150 sets a spatial region 1220 corresponding to the second spatial region 720 with respect to ultrasound image data 1200 including image data representing a tumor 1210. It should be noted that the spatial region 1220 corresponding to the second spatial region 720 does not need to be completely the same as the second spatial region 720 as described according to the first exemplary embodiment. That is, the spatial region corresponding to the second spatial region may be different from the second spatial region to such an extent that it is possible to visually recognize the representation of the second spatial region when the spatial region corresponding to the second spatial region is imaged. For example, in a case where the ultrasound image data is generated by beam forming, the image data of one cross section is typically determined by a focal range of the ultrasonic waves. In a case where this focal range is not matched with an integral multiple of the voxel size of the photoacoustic image data, it is difficult to strictly match the second spatial region 720 with the spatial region 1220 corresponding to the second spatial region 720. From the above-described circumstances, the spatial region to such an extent that it is possible to visually recognize the representation of the ultrasound image data of the second spatial region 720 may be set as the spatial region 1220 corresponding to the second spatial region 720.

Figure 12C:
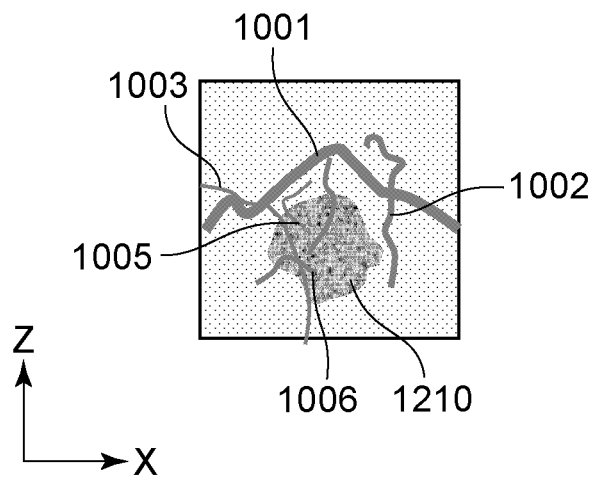
FIG. 12C is a schematic diagram illustrating the image display method according to the second exemplary embodiment.
Figure 12D:
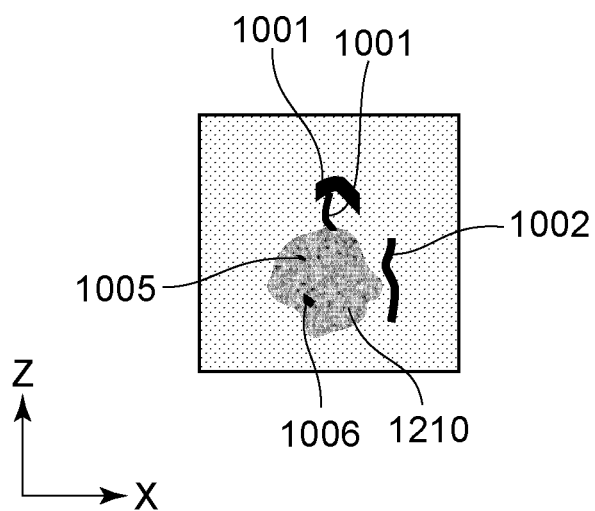
FIG. 12D is a schematic diagram illustrating the image display method according to the second exemplary embodiment.

FIG. 12C illustrates the superimposed image (first superimposed image) generated by superimposing the first photoacoustic image and the ultrasound image (B mode image) on each other. FIG. 12D illustrates the superimposed image (second superimposed image) generated by superimposing the second photoacoustic image and the ultrasound image (B mode image) on each other. According to the present exemplary embodiment, the first photoacoustic image and the second photoacoustic image are blood vessel images where blood vessels including the blood vessels 1001, 1002, and 1003 are depicted. On the other hand, the ultrasound image (B mode image) is a tumor image where the tumor 1210 is depicted. According to the present exemplary embodiment, the ultrasound image is set as the base image, and the first or second photoacoustic image is superimposed on the ultrasound image. When the above-described layer order is adopted, in the first superimposed image, it is possible to easily visually recognize a positional relationship of the entire structure of the blood vessel depicted in the photoacoustic image with respect to the tumor image existing in the ultrasound image. Furthermore, in the second superimposed image, it is possible to easily visually recognize where the local blood vessel image depicted in the second photoacoustic image corresponding to the cross section substantially the same as the ultrasound image is located in the entire structure of the blood vessel. In this manner, it is possible for the user to perform a diagnosis by mutually referring to the information obtained from the first superimposed image and the information obtained from the second superimposed image. As a result, since the second photoacoustic image has information of the spatial region substantially the same as the ultrasound image, it is possible to easily visually recognize whether or not the blood vessel image depicted in the second photoacoustic image is intruding into the tumor image depicted in the ultrasound image by referring to the first photoacoustic image.

In addition, mutual color arrangements are preferably changed such that it is possible to visually recognize the plurality of images constituting the superimposed image while being discriminated from one another. For example, the ultrasound image is displayed in gray scale, and the first photoacoustic image is displayed in color. The second photoacoustic image may be displayed in a different color from that of the first photoacoustic image. That is, the computer 150 may generate the superimposed image by setting a saturation of a medical image (such as an ultrasound image) in the superimposed image to be lower than a saturation of the first or second photoacoustic image. When the display is performed with the above-described color arrangements, since it is possible to additionally display the color photoacoustic image together with the B mode image having a color arrangement (gray scale) that is familiar looking for the doctor while being discriminated from each other, it is possible for the doctor to perform a diagnosis without much sense of discomfort.

It should be noted that it is also possible to perform the change of the viewing direction and the change of the imaging region similarly as in the first exemplary embodiment.

According to the present exemplary embodiment, the image display method at a time when the computer 150 obtains the ultrasound image data including the image data representing the tumor and the photoacoustic image data including the image data representing the blood vessel from the storage unit 152 has been described. It should be noted that the image display method according to the present exemplary embodiment can be appropriately applied to not only a case where the ultrasound image data and the photoacoustic image data are obtained but also a case where the volume data including the image data representing the tumor and the volume data including the image data representing the blood vessel are obtained. For example, at least one of the MRI image data, the X-ray CT image data, the PET image data, the B mode image data, and elastography image data can be adopted as the volume data including the image data representing the tumor. In addition, at least one of the photoacoustic image data, the MR blood vessel imaging method (MRA) image data, the X-ray CT blood vessel imaging method (CTA) image data, and the Doppler image data can be adopted as the volume data including the image data representing the blood vessel.

A case will be considered where the user selects image type desired to be displayed from among a plurality of image types. In this case, the image display method may be changed in accordance with a combination of the selected image types. That is, the computer 150 may determine the image display method on the basis of information indicating the combination of the selected image types. Specifically, the computer 150 determines whether the selected image type includes the image data representing the tumor or includes the image data representing the blood vessel. Subsequently, in a case where the selected image type includes the image data representing the tumor on the basis of the determination result, the computer 150 processes this image data similarly as in the ultrasound image data according to the present exemplary embodiment. On the other hand, in a case where the selected image type includes the image data representing the blood vessel on the basis of the determination result, the computer 150 processes this image data similarly as in the photoacoustic image data according to the present exemplary embodiment. It should be noted that, according to the present exemplary embodiment, the computer 150 determines that the selected image type includes the image data representing the tumor in a case where the selected image type is one of the MRI image data, the X-ray CT image data, the PET image data, the B mode image data, and the elastography image data. On the other hand, the computer 150 determines that the selected image type includes the image data representing the blood vessel in a case where the selected image type is one of the photoacoustic image data, the MR blood vessel imaging method (MRA) image data, the X-ray CT blood vessel imaging method (CTA) image data, and the Doppler image data.

FIG. 13 illustrates a specific example of a graphic user interface (GUI) displayed on the display unit 160.

A display region 1310 is a display region where the parallel image of the first photoacoustic image and the second photoacoustic image is displayed. According to the present exemplary embodiment, the superimposed image (second superimposed image) of the ultrasound image representing the cross section (equivalent to the second spatial region) instructed by the user using the input unit 170 and the photoacoustic image is displayed on the left side in the display region 1310. In addition, the superimposed image (first superimposed image) of the ultrasound image representing the cross section (equivalent to the second spatial region) instructed by the user using the input unit 170 and the first photoacoustic image representing the entire region of the photoacoustic image data is displayed on the right side in the display region 1310.

A display region 1320 is a region where thumbnail images 1321 to 1323 of the parallel images representing a plurality of cross sections generated by the image display method according to the present exemplary embodiment are displayed. The parallel image selected by the user from among the thumbnail images displayed in the display region 1320 is displayed in the display region 1310. In the case of FIG. 13, the thumbnail image 1322 is selected, the parallel image corresponding to the thumbnail image 1322 is displayed in the display region 1310.

It should be noted that, when the image is selected by using the input unit 170 from among the thumbnail images displayed in the display region 1320, the selected thumbnail image may be expanded to be displayed in the display region 1310. For example, while a touch screen is used as the display unit 160, the image to be expanded may be selected by touching one of the thumbnail images 1321 to 1323. The image to be expanded may also be selected by swiping or flicking one of the thumbnail images 1321 to 1323 into the display region 1310.

When the user operates an image feeding icon 1328, the parallel images to be displayed in the display region 1310 can be sequentially switched. It should be noted that, when the image feeding icon 1328 is operated, the thumbnail images displayed in the display region 1320 are also sequentially switched in synchronism with the parallel image displayed in the display region 1310. A rule for the image feeding is not limited to this, and the image feeding may be performed under any rule. The operation instruction of the user with respect to the image feeding icon is equivalent to the switching instruction.

A display region 1330 is a display region where an image for performing a setting of information of an inspection object or a setting of display parameters is displayed. An imaging object site is displayed in a site display region 1331. In the present display example, it is illustrated that the imaging object site is the abdominal region. It should be noted that the imaging object site to be displayed in a site display region 1331 can be set on the basis of information of an inspection order.

The image types of the ultrasound image to be displayed in the display regions 1310 and 1320 are displayed in a type display region 1332. The user can select the image type of the ultrasound image set as the display object by using the input unit 170 from among the plurality of image types displayed in the type display region 1332. In the present display example, a configuration is adopted in which the user can select the ultrasound image from among the B mode image, the Doppler image, and the elastography image. In the present display example, a case is presumed where the B mode image is selected, and the display is performed such that the selection of the B mode image can be identified.

The image types of the photoacoustic image to be displayed in the display regions 1310 and 1320 are displayed in a type display region 1333. The user can select the image type of the photoacoustic image to be displayed by using the input unit 170 from among the plurality of image types displayed in the type display region 1333. In the present display example, a configuration is adopted in which the user can select the photoacoustic image from among an initial sound pressure image, an optical absorption coefficient image, and an oxygen saturation image. In the present display example, a case is presumed where the optical absorption coefficient image is selected, and the display is performed such that the selection of the optical absorption coefficient image can be identified.

It should be noted that the ultrasound image and the photoacoustic image may be displayed on the display unit 160 in mutually different color arrangements. For example, in a case where the ultrasound image and the photoacoustic image are superimposed on each other to be displayed, the color arrangements may be set such that it is facilitated to distinguish the ultrasound image from the photoacoustic image in a manner that the color arrangement of the photoacoustic image is set as a complementary of the ultrasound image or the like. In addition, for example, in a case where the ultrasound image and the photoacoustic image have a pixel value in the same pixel, an overlapped part may be displayed in a color arrangement different from both the ultrasound image and the photoacoustic image. The color arrangement may also be changed when the user clicks a color arrangement changing unit 1334 corresponding to an icon for changing the color arrangement of the ultrasound image or the photoacoustic image by using the input unit 170. Moreover, the color arrangement of the image may be changed in accordance with an instruction of the user other than the click of the color arrangement changing unit 1334 displayed on the display unit 160.

A configuration may be adopted with regard to the superimposed image of the ultrasound image and the photoacoustic image in which transmittances of the respective images can be changed. For example, the transmittance of the ultrasound image or the photoacoustic image may be changed while the user operates a sliding bar 1335 to left or right by using the input unit 170. In the present display example, a configuration is adopted in which the transmittance is changed in accordance with a position of the sliding bar 1335.

In addition, a superimposed image of an image obtained by performing emphasis processing using a signal filter, an image filter, or the like on at least one of the ultrasound image and the photoacoustic image may be displayed. For example, edge emphasis processing may be performed on the ultrasound image, and the ultrasound image having emphasized outlines and the photoacoustic image may be superimposed on each other to be displayed. Blood vessel emphasis processing may be performed on the photoacoustic image, and the photoacoustic image the emphasized blood vessel may be superimposed on the ultrasound image.

It should be noted that, for convenience in the present display example, boundaries of the respective display regions are displayed by using solid lines to be distinguished from one another, but the display of the boundaries may also be avoided.

For example, as illustrated in FIG. 13, a case will be considered where the B mode image is selected from the ultrasound image, and the optical absorption coefficient image is selected from the photoacoustic image as the display image. In this case, the computer 150 determines that the B mode image includes the image data representing the tumor and also determines that the optical absorption coefficient image includes the image data representing the blood vessel. In this case, the computer 150 uses the image display method according to the present exemplary embodiment irrespective of the instruction of the user due to a combination of the volume data including the image data representing the tumor and the volume data including the image data representing the blood vessel. On the other hand, in a case where the user selects only the optical absorption coefficient image, the computer 150 determines that only the volume data including the image data representing the blood vessel is selected and uses the image display method according to the first exemplary embodiment irrespective of the instruction of the user.

Third Exemplary Embodiment

According to a third exemplary embodiment, a mode will be described where an image representing the region of interest is superimposed and displayed in addition to the photoacoustic image described according to the first exemplary embodiment. According to the third exemplary embodiment too, an apparatus similar to the photoacoustic apparatus described according to the first exemplary embodiment is used. The component already described above will be assigned with the same reference sign, and a detailed description thereof will be omitted.

The image display method including information processing according to the present exemplary embodiment will be described with reference to FIG. 14. It should be noted that the respective steps are executed while the computer 150 controls the operations of the components of the photoacoustic apparatus. In addition, a step similar to the step illustrated in FIG. 6 and FIG. 11 will be assigned with the same reference sign, and a detailed description thereof will be omitted.

First, S100 and S200 are executed to move the probe 180 to a specified position.

Subsequently, the probe 180 performs the light irradiation and the reception of the photoacoustic wave (S300 and S400), and the computer 150 generates the photoacoustic image data on the basis of the reception signal of the photoacoustic wave (S500).

<S1100: Step of Obtaining Volume Data Representing Region of Interest>

Subsequently, the computer 150 obtains three-dimensional volume data representing the region of interest (ROI) such as a tumor. The computer 150 may obtain the volume data representing the region of interest by reading out the volume data representing the region of interest previously stored in the storage unit 152.

The computer 150 may also generate the volume data representing the region of interest on the basis of the instruction of the user.

For example, the user may select an arbitrary region from among a plurality of predetermined regions, and the computer 150 may generate the volume data representing the region of interest while the selected region is set as the region of interest.

In addition, the user may specify an arbitrary three-dimensional region representing the tumor region or the like with respect to a medical image displayed on the display unit 160 and generate the volume data representing the region of interest while the region specified by the computer 150 is set as the region of interest. The images such as the photoacoustic image, the MRI image, the X-ray CT image, the PET image, the ultrasound image, and the like obtained by any modality can be adopted as the medical image used for specifying the region of interest. For example, the computer 150 may perform rendering display of the photoacoustic image data, and the user may set the region of interest by using the input unit 170 with respect to the rendering image. The user may also specify the region of interest by using the input unit 170 with respect to the rendering image of the image data obtained by the modality other than the photoacoustic apparatus. At this time, the user may specify an arbitrary region with respect to the rendering image and set the region as the region of interest. Moreover, the user may specify an arbitrary position with respect to the rendering image and set a predetermined range including the specified position as the region of interest. The user may select a predetermined region from among a plurality of regions displayed on the display unit 160 and set the region as the region of interest. The plurality of regions set as the selection targets may be superimposed on the rendering image.

The computer 150 may obtain the volume data representing the region of interest by evaluation a voxel value of the volume data for setting the region of interest. For example, the computer 150 may set a region where the voxel value of the volume data is within a predetermined numeric value range as the region of interest. The computer 150 may also set a region where the voxel value of the volume data is higher than a predetermined threshold as the region of interest.

The computer 150 may also set a plurality of regions of interest and obtain a plurality of pieces of the volume data representing the regions of interest. In addition, the computer 150 may update a superimposed region of the plurality of regions of interest set by a plurality of methods as the final region of interest.

<S1200: Step of Generating and Displaying Superimposed Image Based on Volume Data Representing Region of Interest and Photoacoustic Image Data>

The computer 150 generates the superimposed image of the image of the region of the interest and the photoacoustic image on the basis of the volume data representing the region of interest obtained in S1100 and the photoacoustic image data generated in S500 and causes the display unit 160 to display the superimposed image. The computer 150 generates the first photoacoustic image corresponding to the first spatial region on the basis of the photoacoustic image data. The computer 150 also generates the second photoacoustic image corresponding to the second spatial region on the basis of the photoacoustic image data. Furthermore, the computer 150 generates an image of the region of interest corresponding to the second spatial region on the basis of the volume data representing the region of interest.

Subsequently, the computer 150 generates a superimposed image (third superimposed image) in which the first photoacoustic image and the image of the region of interest are superimposed on each other. In addition, the computer 150 generates a superimposed image (fourth superimposed image) in which the second photoacoustic image and the image of the region of interest are superimposed on each other. The computer 150 displays the third superimposed image and the fourth superimposed image while being assigned side by side on the display unit 160.

Figure 15A:
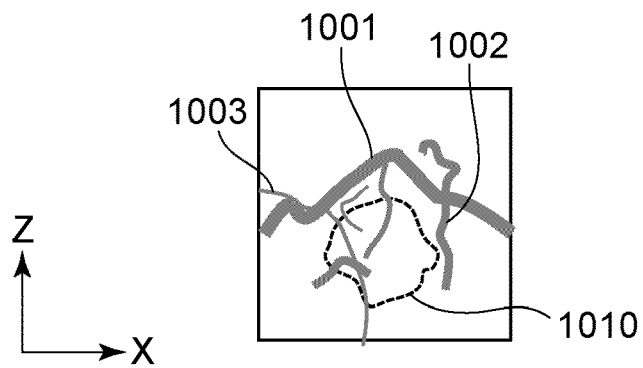
FIG. 15A illustrates a display example of the parallel image according to the third exemplary embodiment.
Figure 15B:
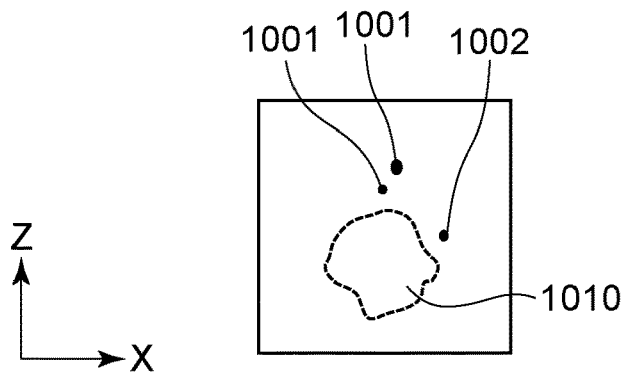
FIG. 15B illustrates a display example of the parallel image according to the third exemplary embodiment.
Figure 15C:
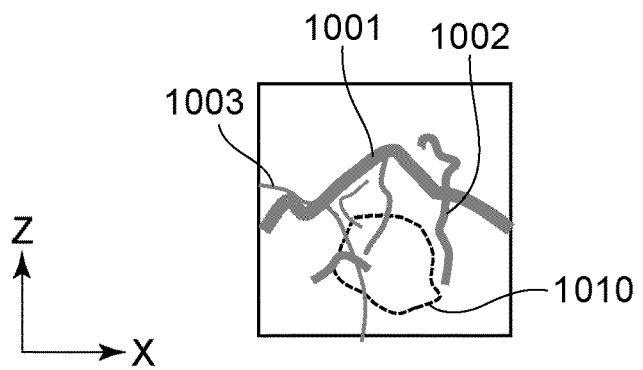
FIG. 15C illustrates a display example of the parallel image according to the third exemplary embodiment.
Figure 15D:
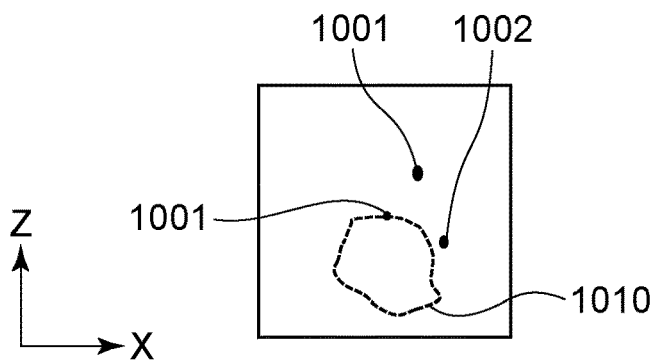
FIG. 15D illustrates a display example of the parallel image according to the third exemplary embodiment.

As illustrated in FIG. 15A, the computer 150 may also generate an image in which the first photoacoustic image is set as the base image and the image of the region of interest is superimposed on the first photoacoustic image as the third superimposed image. In addition, as illustrated in FIG. 15B, the computer 150 may generate an image in which the image of the region of interest is set as the base image, and the second photoacoustic image is superimposed on the image of the region of interest as the fourth superimposed image. When the above-described layer order is adopted, for example, the region of interest does not submerge into the entire structure of the blood vessel depicted in the first photoacoustic image, and it is possible to check the second photoacoustic image for checking the intrusion of the blood vessel into the region of interest without being concealed by the region of interest. In FIGS. 15A to 15D, an outer edge of the region of interest 1510 is illustrated by a dotted line. In addition, FIG. 15C and FIG. 15D illustrate images in a case where the photoacoustic image data of the second spatial region and the volume data representing the region of interest are represented which are different from FIG. 15A and FIG. 15B.

The image of the region of interest and the photoacoustic image may be displayed in mutually different color arrangements on the display unit 160. For example, the computer 150 may display the first or second photoacoustic image in gray scale and display the image of the region of interest in color. The second photoacoustic image may also be displayed by using a color different from that of the image of the region of interest. In addition, for example, in a case where a pixel value exists in the same pixel in the image of the region of interest and the second photoacoustic image, the overlapped part may be displayed in a color arrangement different from those of both the image of the region of interest and the second photoacoustic image.

The color arrangements may be changed inside and outside the region of interest with regard to the second photoacoustic image with regard to the second photoacoustic image. That is, the color arrangement with regard to the second photoacoustic image 1501 (blood vessel image) located inside the region of interest 1510 may be different from the color arrangement of the second photoacoustic images 1502 and 1503 located outside the region of interest 1510. With this configuration, it is possible to easily discriminate the blood vessel intruding into the region of interest from the blood vessel that is not intruding into the region of interest. It should be noted that the blood vessel intruding into the region of interest may be easily discriminated from the blood vessel that is not intruding into the region of interest while the display modes of the second photoacoustic image inside and outside the region of interest are changed by a method other than the change of the color arrangements. For example, a display mode for flashing the second photoacoustic image existing within the region of interest or a display mode for performing a notification by a text that the image exists within the region of interest may be adopted.

Figure 16A:
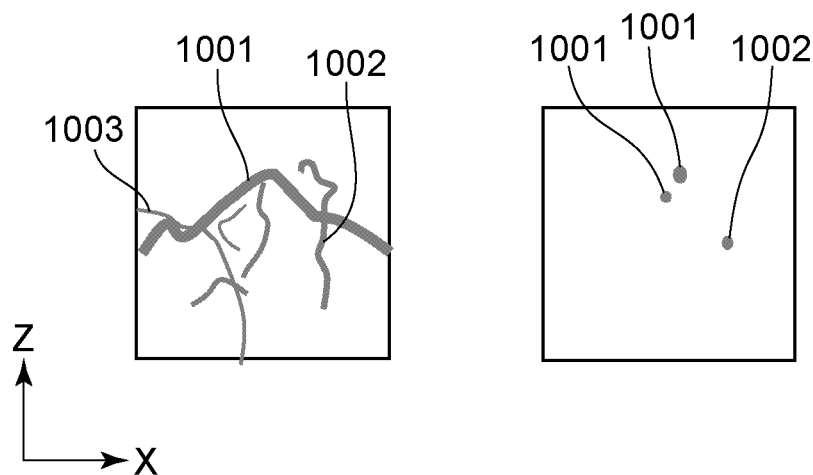
FIG. 16A illustrates another display example of the parallel image according to the third exemplary embodiment.
Figure 16B:
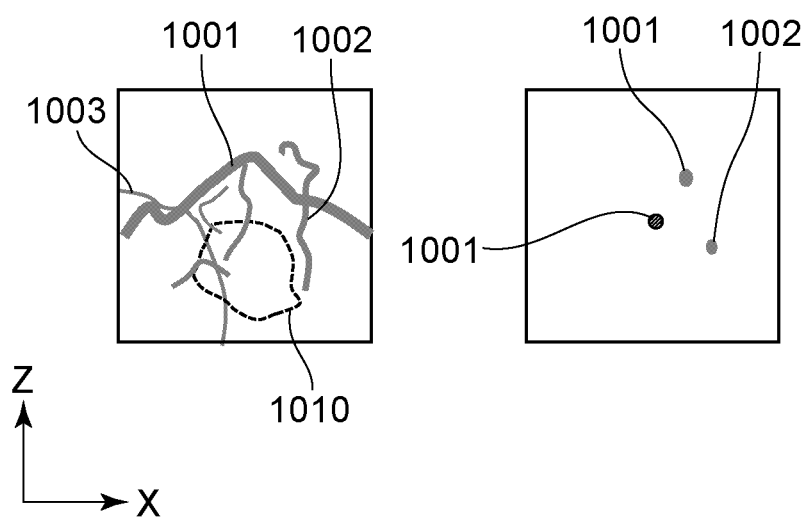
FIG. 16B illustrates another display example of the parallel image according to the third exemplary embodiment.

It should be noted that, as illustrated in FIGS. 16A and 16B, the computer 150 may change the display modes of the second photoacoustic image inside and outside the region of interest to be displayed on the basis of the volume data representing the region of interest and the photoacoustic image data without displaying the image of the region of interest. FIGS. 16A and 16B illustrate the parallel images in a case where the mutually different photoacoustic image data of the second spatial region are represented. In this case too, any display mode changes such as the flashing and the text notification can be performed in addition to the change of the color arrangements. With this configuration, it is possible for the user to easily discriminate whether the second photoacoustic image exists inside or outside the region of interest.

It should be noted that the second photoacoustic image overlapped with the region of interest 1510 and the second photoacoustic image located inside the region of interest 1510 may be displayed in the same display mode. That is, the second photoacoustic image overlapped with the region of interest 1510 and the second photoacoustic image located outside the region of interest 1510 may be displayed in different display modes. In addition, the second photoacoustic image located inside the region of interest 1510, the second photoacoustic image overlapped with the region of interest 1510, and the second photoacoustic image located outside the region of interest 1510 may be displayed in mutually different display modes.

A diagnosis by checking a situation where the region of interest such as the tumor is intruding into the blood vessel is presumed as an image diagnosis using the volume data including the image data representing the blood vessel. In view of the above, the second photoacoustic image where it is determined that the blood vessel is intruding into the region of interest may be displayed as an image displayed by default when the volume data is read.

Specifically, first, the computer 150 specifies a position (for example, a cross section) of the photoacoustic image data where the voxel value at the boundary of the region of interest is within a predetermined numeric value range (for example, the voxel value higher than or equal to a certain threshold) on the basis of the photoacoustic image data and the volume data representing the region of interest. The computer 150 selects the image constituted by the second photoacoustic image including the photoacoustic image data where the voxel value at the boundary of the region of interest is within the predetermined range. Subsequently, the computer 150 displays the selected superimposed image at the beginning. With this configuration, since the doctor can first check the image representing the situation where the blood vessel is intruding into the region of interest, a diagnosis efficiency is improved.

In a case where the display is performed while the computer 150 automatically sequentially switch the parallel images, it is also possible to lengthen a time interval for switching the parallel images before and after the image where it is determined that the blood vessel is intruding into the region of interest.

Specifically, the computer 150 selects the parallel image constituted by the second photoacoustic image including the photoacoustic image data where the voxel value at the boundary of the region of interest is within the predetermined range by using the above-described method. Furthermore, the computer 150 selects a parallel image group spatially located in the vicinity of the selected parallel image (for example, the parallel images in 10 frames before and after the selected parallel image). Subsequently, the computer 150 sequentially switches the parallel image group including the selected parallel image group to be displayed. At this time, when the display of the selected parallel image group is switched, the switching time is lengthened as compared with the switching of the other parallel image group.

With this configuration, the doctor can take relatively long time to check the parallel image representing the situation where the blood vessel is intruding into the region of interest, and, on the other hand, the redundant parallel image where the blood vessel is not intruding into the region of interest is swiftly switched. Thus, the diagnosis efficiency is improved.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2017-094994, filed May 11, 2017, which is hereby incorporated by reference herein in its entirety.

The invention claimed is:
1. An image display method comprising:
obtaining photoacoustic image data representing volume data generated on the basis of a reception signal of a photoacoustic wave;
generating a first photoacoustic image corresponding to a first spatial region on the basis of the photoacoustic image data;
generating a second photoacoustic image corresponding to a second spatial region having a different thickness from a thickness of the first spatial region in a viewing direction of rendering and having a spatial region overlapped with the first spatial region on the basis of the photoacoustic image data; and
displaying a parallel image in which the first photoacoustic image and the second photoacoustic image are arranged,
wherein, in the case where the viewing direction of rendering to the photoacoustic image data is change, the first photoacoustic image based on the photoacoustic image data is updated based on the changed viewing direction, and the second photoacoustic image based on the photoacoustic image is updated based on the changed viewing direction.

2. The image display method according to claim 1, wherein the thickness of the second spatial region in the viewing direction is smaller than the thickness of the first spatial region in the viewing direction.

3. The image display method according to claim 2, wherein the second spatial region is a partial spatial region of the first spatial region.

4. The image display method according to claim 1, wherein an entire region of the photoacoustic image data is set as the first spatial region.

5. The image display method according to claim 1,
wherein medical image data obtained by a modality different from a photoacoustic apparatus is obtained,
wherein a medical image corresponding to a region corresponding to the second spatial region is generated on the basis of the medical image data,
wherein a first superimposed image in which the medical image and the first photoacoustic image are superimposed on each other is generated,
wherein a second superimposed image in which the medical image and the second photoacoustic image are superimposed on each other is generated, and
wherein the parallel image in which the first superimposed image including the first photoacoustic image and the second superimposed image including the second photoacoustic image are arranged side by side is generated and displayed.

6. The image display method according to claim 5,
wherein the first superimposed image in which the first photoacoustic image is superimposed on the medical image is generated, and
wherein the second superimposed image in which the second photoacoustic image is superimposed on the medical image is generated.

7. The image display method according to claim 5,
wherein a saturation of the medical image in the first superimposed image is set to be lower than a saturation of the first photoacoustic image, and
wherein a saturation of the medical image in the second superimposed image is set to be lower than a saturation of the second photoacoustic image.

8. The image display method according to claim 5, wherein the medical image data is ultrasound image data derived from a reflection wave of an ultrasonic wave transmitted to an object.

9. The image display method according to claim 1,
wherein volume data representing a region of interest is obtained,
wherein an image of the region of interest corresponding to the second spatial region is generated on the basis of the volume data representing the region of interest,
wherein a third superimposed image in which the image of the region of interest and the first photoacoustic image are superimposed on each other is generated,
wherein a fourth superimposed image in which the image of the region of interest and the second photoacoustic image are superimposed on each other is generated, and
wherein the parallel image in which the third superimposed image including the first photoacoustic image and the fourth superimposed image including the second photoacoustic image are arranged side by side is generated and displayed.

10. The image display method according to claim 9,
wherein the thickness of the second spatial region in the viewing direction is smaller than the thickness of the first spatial region in the viewing direction,
wherein the third superimposed image in which the image of the region of interest is superimposed on the first photoacoustic image is generated, and
wherein the fourth superimposed image in which the second photoacoustic image is superimposed on the image of the region of interest is generated.

11. The image display method according to claim 9, wherein color arrangements of the second photoacoustic image inside and outside the region of interest are changed.

12. The image display method according to claim 1,
wherein volume data representing a region of interest is obtained, and
wherein color arrangements of the second photoacoustic image inside and outside the region of interest are changed.

13. The image display method according to claim 1, wherein a position of the first spatial region and a position of the second spatial region are changed in synchronism with each other on the basis of an instruction of a user, and the parallel image is generated by updating the first photoacoustic image and the second photoacoustic image to represent the changed first spatial region and the changed second spatial region.

14. The image display method according to claim 1, wherein a position of the second spatial region is changed on the basis of an instruction of a user, a position of the first spatial region is not changed on the basis of the instruction, and the second photoacoustic image is updated to represent the changed second spatial region to be displayed.

15. The image display method according to claim 1,
wherein the first photoacoustic image corresponding to the first spatial region is generated by setting an opacity of the first spatial region to be higher than an opacity of a spatial region except for the first spatial region, and
wherein the second photoacoustic image corresponding to the second spatial region is generated by setting an opacity of the second spatial region to be higher than an opacity of a spatial region except for the second spatial region.

16. The image display method according to claim 1,
wherein the rendering of the photoacoustic image data is performed while the spatial region except for the first spatial region is excluded from a rendering target to generate the first photoacoustic image representing the first spatial region, and
wherein the rendering of the photoacoustic image data is performed while the spatial region except for the second spatial region is excluded from a rendering target to generate the second photoacoustic image corresponding to the second spatial region.

17. The image display method according to claim 1, wherein the first photoacoustic image and the second photoacoustic image are generated by a rendering technique of the same type.

18. The image display method according to claim 17, wherein the first photoacoustic image and the second photoacoustic image are generated by performing volume rendering with respect to the photoacoustic image data.

19. The image display method according to claim 17, wherein the first photoacoustic image and the second photoacoustic image are generated by performing maximum intensity projection of the photoacoustic image data.

20. A non-transitory computer-readable medium storing a program that causes a computer to execute the image display method according to claim 1.

21. A display control apparatus comprising:
- an image data obtaining unit configured to obtain photoacoustic image data representing volume data generated on the basis of a reception signal of a photoacoustic wave; and
- a display control unit configured to generate a first photoacoustic image corresponding to a first spatial region on the basis of the photoacoustic image data and generate a second photoacoustic image corresponding to a second spatial region having a different thickness from a thickness of the first spatial region in a viewing direction of rendering and having a spatial region overlapped with the first spatial region on the basis of the photoacoustic image data, and
- arrange the first photoacoustic image and the second photoacoustic image to obtain an image and cause a display unit to display the image,
- wherein, in the case where the viewing direction of rendering to the photoacoustic image data is change, the first photoacoustic image based on the photoacoustic image data is updated based on the changed viewing direction, and the second photoacoustic image based on the photoacoustic image is updated based on the changed viewing direction.

22. The display control apparatus according to claim 21, wherein the image data obtaining unit is configured to obtain the photoacoustic image data by reading out the photoacoustic image data stored in a storage unit.

* * * * *